United States Patent
Stahl et al.

(10) Patent No.: US 11,511,130 B2
(45) Date of Patent: Nov. 29, 2022

(54) SYSTEMS AND METHODS FOR ADJUSTING MULTI-LEAF COLLIMATOR

(71) Applicant: SHANGHAI UNITED IMAGING HEALTHCARE CO., LTD., Shanghai (CN)

(72) Inventors: Johannes Stahl, Houston, TX (US); Walter Arturo Aguilar, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 135 days.

(21) Appl. No.: 16/848,857

(22) Filed: Apr. 15, 2020

(65) Prior Publication Data

US 2021/0322787 A1  Oct. 21, 2021

(51) Int. Cl.
*A61N 5/10* (2006.01)
*G21K 1/04* (2006.01)
*G21K 1/02* (2006.01)

(52) U.S. Cl.
CPC ............ *A61N 5/1045* (2013.01); *A61N 5/10* (2013.01); *A61N 5/103* (2013.01); *A61N 5/1031* (2013.01);
(Continued)

(58) Field of Classification Search
CPC ........ A61N 5/10; A61N 5/103; A61N 5/1031; A61N 5/1036; A61N 5/1042;
(Continued)

(56) References Cited

U.S. PATENT DOCUMENTS 5,039,867 A * 8/1991 Nishihara ............ A61N 5/1042
250/492.3
5,591,983 A * 1/1997 Yao .......................... G21F 5/04
250/505.1
(Continued)

FOREIGN PATENT DOCUMENTS

CN   102755696 A   10/2012
CN   104835547 A   8/2015
(Continued)

OTHER PUBLICATIONS

First Office Action in Chinese Application No. 202110345738.1 dated May 31, 2022, 11 pages.

*Primary Examiner* — Allen C. Ho
(74) *Attorney, Agent, or Firm* — Metis IP LLC

(57) ABSTRACT

The disclosure provides systems and methods for adjusting a multi-leaf collimator (MLC). The MLC includes a plurality of cross-layer leaf pairs, each cross-layer leaf pair of the plurality of cross-layer leaf pairs includes a first leaf located in a first layer of leaves and a second leaf opposingly located in a second layer of leaves. For at least one cross-layer leaf pair, an effective cross-layer leaf gap to be formed between the first leaf and the second leaf may be determined; at least one of the first leaf or the second leaf may be caused to move to form the effective cross-layer leaf gap; and an in-layer leaf gap may be caused, based on the effective cross-layer leaf gap, to be formed between the first leaf and an opposing first leaf in the first layer. A size of the in-layer leaf gap may be no less than a threshold.

20 Claims, 8 Drawing Sheets

(52) U.S. Cl.
CPC ......... *A61N 5/1036* (2013.01); *A61N 5/1042* (2013.01); *A61N 5/1043* (2013.01); *A61N 5/1044* (2013.01); *A61N 5/1047* (2013.01); *A61N 5/1048* (2013.01); *A61N 5/1064* (2013.01); *A61N 5/1065* (2013.01); *A61N 5/1067* (2013.01); *A61N 5/1077* (2013.01); *A61N 5/1081* (2013.01); *G21K 1/02* (2013.01); *G21K 1/025* (2013.01); *G21K 1/04* (2013.01); *G21K 1/043* (2013.01); *G21K 1/046* (2013.01)

(58) Field of Classification Search
CPC .. A61N 5/1043; A61N 5/1044; A61N 5/1045; A61N 5/1047; A61N 5/1064; A61N 5/1065; A61N 5/1067; A61N 5/1048; A61N 5/1077; A61N 5/1081; G21K 1/02; G21K 1/025; G21K 1/04; G21K 1/043; G21K 1/046
USPC ...................... 378/65 and, 151–153, 65, 147
See application file for complete search history.

(56) References Cited

U.S. PATENT DOCUMENTS

| | | | | |
|---|---|---|---|---|
| 5,847,403 | A * | 12/1998 | Hughes | G21F 5/04 378/150 |
| 6,108,400 | A * | 8/2000 | Siochi | A61N 5/1031 378/147 |
| 6,266,393 | B1 * | 7/2001 | Ein-Gal | A61N 5/1042 250/505.1 |
| 6,322,249 | B1 * | 11/2001 | Wofford | A61N 5/1049 378/152 |
| 6,526,123 | B2 * | 2/2003 | Ein-Gal | A61N 5/1042 250/505.1 |
| 6,600,810 | B1 * | 7/2003 | Hughes | G21K 1/04 378/147 |
| 6,647,092 | B2 * | 11/2003 | Eberhard | G21K 1/04 378/150 |
| 6,711,237 | B1 * | 3/2004 | Schlegel | G21K 1/04 378/150 |
| 6,757,355 | B1 * | 6/2004 | Siochi | A61N 5/1042 378/147 |
| 6,760,402 | B2 * | 7/2004 | Ghelmansarai | A61N 5/1049 378/65 |
| 6,853,705 | B2 * | 2/2005 | Chang | G21K 1/046 378/65 |
| 6,907,105 | B2 * | 6/2005 | Otto | A61N 5/1042 378/151 |
| 6,999,556 | B2 * | 2/2006 | Nakano | A61N 5/103 378/152 |
| 8,009,794 | B2 * | 8/2011 | Partain | A61B 6/035 378/7 |
| 8,249,215 | B2 * | 8/2012 | Vaitheeswaran | A61N 5/1042 378/65 |
| 8,331,532 | B2 * | 12/2012 | Nord | G21K 1/046 378/65 |
| 8,467,499 | B2 * | 6/2013 | Furth | A61N 5/1042 378/152 |
| 8,509,383 | B2 * | 8/2013 | Lu | A61N 5/1049 378/65 |
| 8,637,841 | B2 * | 1/2014 | Prince | A61N 5/1045 250/492.1 |
| 8,718,234 | B2 * | 5/2014 | Echner | G21K 1/04 378/152 |
| 8,767,917 | B2 * | 7/2014 | Ruchala | A61N 5/103 378/65 |
| 8,824,638 | B2 * | 9/2014 | Nicholson | A61B 6/06 378/150 |
| 8,847,179 | B2 * | 9/2014 | Fujitaka | A61N 5/1036 250/492.1 |
| 8,917,816 | B2 * | 12/2014 | Ji | G21K 1/046 378/152 |
| 8,938,051 | B2 * | 1/2015 | Broad | A61N 5/1045 378/152 |
| 10,398,911 | B2 * | 9/2019 | Nord | G21K 1/046 |
| 10,420,958 | B2 * | 9/2019 | Kauppinen | G21K 1/046 |
| 10,434,334 | B2 * | 10/2019 | Wang | A61N 5/1036 |
| 10,441,814 | B2 * | 10/2019 | Nord | A61N 5/1036 |
| 10,500,417 | B2 * | 12/2019 | Kuusela | A61N 5/103 |
| 10,709,905 | B2 * | 7/2020 | Hernandez | A61N 5/1047 |
| 10,888,713 | B2 * | 1/2021 | Rieger | G21K 1/043 |
| 10,892,064 | B2 * | 1/2021 | Stahl | A61N 5/1045 |
| 10,960,229 | B2 * | 3/2021 | Ni | A61B 5/055 |
| 10,987,523 | B2 * | 4/2021 | Sheng | A61N 5/1036 |
| 11,000,706 | B2 * | 5/2021 | Kawrykow | A61N 5/1045 |
| 11,331,517 | B2 * | 5/2022 | Liu | A61N 5/1048 |
| 2004/0013237 | A1 | 1/2004 | Brown et al. | |

FOREIGN PATENT DOCUMENTS

| | | |
|---|---|---|
| CN | 207980187 U | 10/2018 |
| CN | 110755762 A | 2/2020 |

* cited by examiner

SYSTEMS AND METHODS FOR ADJUSTING MULTI-LEAF COLLIMATOR

TECHNICAL FIELD

The present disclosure generally relates to a multi-leaf collimator, and more particularly to systems and methods for adjusting a multi-leaf collimator.

BACKGROUND

Radiation therapy has been widely employed in cancer treatment in which ionizing radiation is guided towards a treatment region (e.g., a tumor) of an object. In radiation therapy, high-energy electromagnetic radiation beams and/or particles are delivered for killing or inhibiting the growth of undesired tissue. Generally, it is desirable to delimit the radiation rays so that the radiation dose is maximized in the treatment region and minimized in the healthy tissue of the object. A multi-leaf collimator (MLC) plays an important role in delimiting the radiation rays. An MLC can have a plurality of leaf pairs. Leaves and/or a drive mechanism of the MLC may become damaged by a collision between opposing leaf ends, and thus, care needs to be taken to avoid collisions between opposing leaf ends. To this end, a minimum gap may be maintained between opposing leaves when the leaves move. However, this gap may be undesirable for radiation treatment, because the dose passing through the gap may reach the tissue, resulting in an actual dose higher than planned. Therefore, it is desirable to provide methods and systems for adjusting the MLC of a radiation delivery device, and/or reducing or eliminating an effect of radiation leakage through a leaf gap in radiation with MLC.

SUMMARY

In one aspect of the present disclosure, a method for adjusting a multi-leaf collimator (MLC) in a treatment process is provided. The MLC may include a plurality of cross-layer leaf pairs each of which includes a first leaf located in a first layer of leaves and a second leaf oppositely located in a second layer of leaves. The method may be implemented on at least one machine each of which has at least one processor and at least one storage device. The method may include: for each of at least one of the plurality of cross-layer leaf pairs, determining, according to a treatment plan, an effective cross-layer leaf gap to be formed between the first leaf in the first layer and the second leaf in the second layer; causing at least one of the first leaf or the second leaf to move to form the effective cross-layer leaf gap; and causing, based on the effective cross-layer leaf gap, an in-layer leaf gap to be formed between the first leaf and an opposing first leaf that form an in-layer leaf pair in the first layer. A size of the in-layer leaf gap may be no less than a threshold.

In some embodiments, for the each cross-layer leaf pair, the causing, based on the effective cross-layer leaf gap, an in-layer leaf gap to be formed between the first leaf and an opposing first leaf that form an in-layer leaf pair in the first layer may include: comparing a size of the effective cross-layer leaf gap with 0.

In some embodiments, for the each cross-layer leaf pair, the causing, based on the effective cross-layer leaf gap, an in-layer leaf gap to be formed between the first leaf and an opposing first leaf that form an in-layer leaf pair in the first layer may further include: in response to determining that the size of the effective cross-layer leaf gap is equal to 0, comparing the size of the in-layer leaf gap with the threshold; and in response to determining that the size of the in-layer leaf gap is less than the threshold, causing the in-layer leaf gap to be adjusted to no less than the threshold, by causing the opposing first leaf of the in-layer leaf pair in the first layer to move relative to the first leaf.

In some embodiments, for the each cross-layer leaf pair, the causing, based on the effective cross-layer leaf gap, an in-layer leaf gap to be formed between the first leaf and an opposing first leaf that form an in-layer leaf pair in the first layer may further include: in response to determining that the size of the effective cross-layer leaf gap is equal to 0, comparing the size of the in-layer leaf gap with the threshold; and in response to determining that the size of the in-layer leaf gap is less than the threshold, causing the in-layer leaf gap to be adjusted to no less than the threshold and no larger than a second threshold, by causing the opposing first leaf of the in-layer leaf pair in the first layer to move relative to the first leaf.

In some embodiments, for the each cross-layer leaf pair, the causing, based on the effective cross-layer leaf gap, an in-layer leaf gap to be formed between the first leaf and an opposing first leaf that form an in-layer leaf pair in the first layer may further include: in response to determining that the size of the effective cross-layer leaf gap is larger than 0, comparing the size of the effective cross-layer leaf gap with the threshold; and in response to determining that the size of the effective cross-layer leaf gap is no larger than the threshold, causing the in-layer leaf gap to be adjusted to no less than the threshold, by causing the opposing first leaf of the in-layer leaf pair in the first layer to move relative to the first leaf.

In some embodiments, for the each cross-layer leaf pair, the causing, based on the effective cross-layer leaf gap, an in-layer leaf gap to be formed between the first leaf and an opposing first leaf that form an in-layer leaf pair in the first layer may further include: in response to determining that the size of the effective cross-layer leaf gap is larger than 0, comparing the size of the effective cross-layer leaf gap with the threshold; and in response to determining that the size of the effective cross-layer leaf gap is larger than the threshold, causing the in-layer leaf gap to be adjusted to no less than the effective cross-layer leaf gap, by causing the opposing first leaf of the in-layer leaf pair in the first layer to move relative to the first leaf.

In some embodiments, for the each cross-layer leaf pair, the causing, based on the effective cross-layer leaf gap, an in-layer leaf gap to be formed between the first leaf and an opposing first leaf that form an in-layer leaf pair in the first layer may further include: in response to determining that the size of the effective cross-layer leaf gap is larger than 0, comparing the size of the effective cross-layer leaf gap with the threshold; and in response to determining that the size of the effective cross-layer leaf gap is no larger than the threshold, causing the in-layer leaf gap to be adjusted to no less than the threshold and no larger than a second threshold, by causing the opposing first leaf of the in-layer leaf pair in the first layer to move relative to the first leaf.

In some embodiments, for the each cross-layer leaf pair, the causing, based on the effective cross-layer leaf gap, an in-layer leaf gap to be formed between the first leaf and an opposing first leaf that form an in-layer leaf pair in the first layer may further include: in response to determining that the size of the effective cross-layer leaf gap is larger than 0, comparing the size of the effective cross-layer leaf gap with the threshold and a second threshold; and in response to determining that the size of the effective cross-layer leaf gap is larger than the threshold but no larger than the second threshold, causing the in-layer leaf gap to be adjusted to no less than the effective cross-layer leaf gap and no larger than the second threshold, by causing the opposing first leaf of the in-layer leaf pair in the first layer to move relative to the first leaf.

In some embodiments, for the each cross-layer leaf pair, the causing, based on the effective cross-layer leaf gap, an in-layer leaf gap to be formed between the first leaf and an opposing first leaf that form an in-layer leaf pair in the first layer may further include: in response to determining that the size of the effective cross-layer leaf gap is larger than 0, comparing the size of the effective cross-layer leaf gap with a second threshold; and in response to determining that the size of the effective cross-layer leaf gap is larger than the second threshold, causing the in-layer leaf gap to be adjusted to no less than the effective cross-layer leaf gap, by causing the opposing first leaf of the in-layer leaf pair in the first layer to move relative to the first leaf.

In some embodiments, the method may further include: causing, based on the effective cross-layer leaf gap, a second in-layer leaf gap to be formed between the second leaf and an opposing second leaf that form a second in-layer leaf pair in the second layer.

In some embodiments, the causing, based on the effective cross-layer leaf gap, a second in-layer leaf gap to be formed between the second leaf and an opposing second leaf that form a second in-layer leaf pair in the second layer may include: in response to determining that the size of the effective cross-layer leaf gap is larger than 0, comparing the size of the effective cross-layer leaf gap with the threshold; in response to determining that the size of the effective cross-layer leaf gap is no larger than the threshold, causing the second in-layer leaf gap to be adjusted to no less than the threshold, by causing the opposing second leaf of the second in-layer leaf pair in the second layer to move relative to the second leaf; and causing the in-layer leaf gap to be adjusted to no less than the threshold, by causing the opposing first leaf of the in-layer leaf pair in the first layer to move relative to the first leaf.

In some embodiments, the causing, based on the effective cross-layer leaf gap, a second in-layer leaf gap to be formed between the second leaf and an opposing second leaf that form a second in-layer leaf pair in the second layer may include: in response to determining that the size of the effective cross-layer leaf gap is larger than 0, comparing the size of the effective cross-layer leaf gap with the threshold; in response to determining that the size of the effective cross-layer leaf gap is larger than the threshold, causing the second in-layer leaf gap to be adjusted to no less than the effective cross-layer leaf gap, by causing the opposing second leaf of the second in-layer leaf pair in the second layer to move relative to the second leaf; and causing the in-layer leaf gap to be adjusted to no less than the effective cross-layer leaf gap, by causing the opposing first leaf of the in-layer leaf pair in the first layer to move relative to the first leaf.

In some embodiments, the method may further include: for the each cross-layer leaf pair, causing at least one of the in-layer leaf pair in the first layer or the second in-layer leaf pair in the second layer to be adjusted before or during the treatment process by: causing, based on at least one of the in-layer leaf gap or the second in-layer leaf gap, the in-layer leaf pair in the first layer and the second in-layer leaf pair in the second layer to be adjusted synchronously.

In some embodiments, the method may further include: for the each cross-layer leaf pair, causing the in-layer leaf pair in the first layer to be adjusted before or during the treatment process.

In some embodiments, the threshold may be larger than 0.

In some embodiments, the threshold may be within a range from 0.1 to 2 millimeters.

In some embodiments, the threshold may be within a range from 0.2 to 0.5 millimeters.

In some embodiments, in response to determining that the size of the effective cross-layer leaf gap is equal to 0, the in-layer leaf gap may be no larger than a second threshold.

In some embodiments, the second threshold may be within a range from 2 to 3 millimeters.

In another aspect of the present disclosure, a system for adjusting a multi-leaf collimator (MLC) in a treatment process is provided. The MLC may include a plurality of cross-layer leaf pairs each of which includes a first leaf located in a first layer of leaves and a second leaf opposingly located in a second layer of leaves, The system may include: a drive mechanism configured to drive the plurality of cross-layer leaf pairs to move; and a controller. The controller may be configured to: for each of at least one of the plurality of cross-layer leaf pairs, determining, according to a treatment plan, an effective cross-layer leaf gap to be formed between the first leaf in the first layer and the second leaf in the second layer; causing at least one of the first leaf or the second leaf to move to form the effective cross-layer leaf gap; and causing, based on the effective cross-layer leaf gap, an in-layer leaf gap to be formed between the first leaf and an opposing first leaf that form an in-layer leaf pair in the first layer. A size of the in-layer leaf gap may be no less than a threshold.

In another aspect of the present disclosure, a system for adjusting a multi-leaf collimator (MLC) in a treatment process is provided. The MLC may include a plurality of cross-layer leaf pairs each of which includes a first leaf located in a first layer of leaves and a second leaf opposingly located in a second layer of leaves. The system may include: at least one storage device storing a set of instructions; and at least one processor in communication with the storage device, wherein when executing the set of instructions, the at least one processor may be configured to cause the system to perform operations. The operations may include: for each of at least one of the plurality of cross-layer leaf pairs, determining, according to a treatment plan, an effective cross-layer leaf gap to be formed between the first leaf in the first layer and the second leaf in the second layer; causing at least one of the first leaf or the second leaf to move to form the effective cross-layer leaf gap; and causing, based on the effective cross-layer leaf gap, an in-layer leaf gap to be formed between the first leaf and an opposing first leaf that form an in-layer leaf pair in the first layer. A size of the in-layer leaf gap may be no less than a threshold.

In another aspect of the present disclosure, a non-transitory computer readable medium storing instructions is provided. The instructions, when executed by at least one processor, may cause the at least one processor to implement a method comprising: for each of at least one of the plurality of cross-layer leaf pairs, determining, according to a treatment plan, an effective cross-layer leaf gap to be formed between the first leaf in the first layer and the second leaf in the second layer; causing at least one of the first leaf or the second leaf to move to form the effective cross-layer leaf gap; and causing, based on the effective cross-layer leaf gap, an in-layer leaf gap to be formed between the first leaf and an opposing first leaf that form an in-layer leaf pair in the first layer. A size of the in-layer leaf gap may be no less than a threshold.

In another aspect of the present disclosure, a system is provided. The system may include a multi-leaf collimator (MLC). The MLC may include a plurality of cross-layer leaf pairs each of which includes a first leaf located in a first layer of leaves and a second leaf opposingly located in a second layer of leaves. For each of at least one of the plurality of cross-layer leaf pairs, an effective cross-layer leaf gap may be formed between the first leaf in the first layer and the second leaf in the second layer; an in-layer leaf gap may be formed between the first leaf and an opposing first leaf that form an in-layer leaf pair in the first layer; and a size of the in-layer leaf gap may be no less than the effective cross-layer leaf gap.

In some embodiments, the size of the in-layer leaf gap may be no less than a first threshold and no larger than a second threshold.

In some embodiments, the size of the in-layer leaf gap may be determined based on a random value.

In some embodiments, the size of the in-layer leaf gap may have a fixed value when a size of the effective cross-layer leaf gap is 0.

In some embodiments, the size of the in-layer leaf gap may be equal to a sum of a fixed value and a size of the effective cross-layer leaf gap.

In some embodiments, the size of the in-layer leaf gap may be equal to a size of the effective cross-layer leaf gap when the size of the effective cross-layer leaf gap is no less than a third threshold.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof. It will be understood that the term "object" and "subject" may be used interchangeably as a reference to a thing that undergoes a treatment and/or an imaging procedure in a radiation system of the present disclosure.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Figure 2:
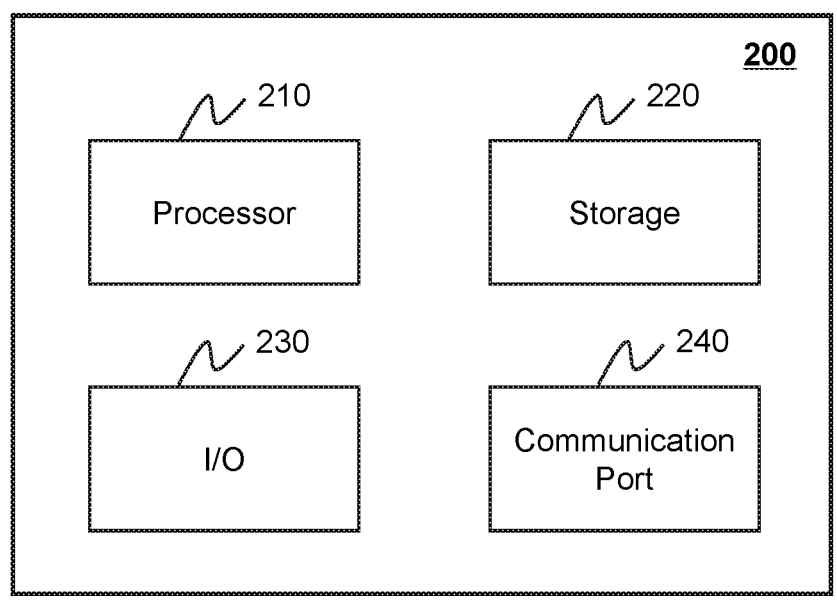
FIG. 2 is a schematic diagram illustrating exemplary hardware and/or software components of an exemplary computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood, the operations of the flowcharts may be implemented not in order. Conversely, the operations may be implemented in inverted order, or synchronously. Moreover, one or more other operations may be added to the flowcharts. One or more operations may be removed from the flowcharts.

The present disclosure relates to systems and methods for adjusting a multi-leaf collimator (MLC) of a radiation delivery device, and/or reducing or eliminating an effect of radiation leakage through a leaf gap in radiation with MLC. When leaves in an MLC move, the leaves or a drive mechanism of the MLC may become damaged by a collision between opposing leaf ends, and thus, care needs to be taken to avoid collisions between opposing leaf ends. To this end, a minimum gap may be maintained between opposing leaves in a same layer when the leaves move. However, this gap may be undesirable for radiation treatment, because it can allow a dose higher than planned to be delivered to the tissue underneath the gap. According to some embodiments of the present disclosure, a multi-layer MLC (e.g., a dual layer MLC) may be used. When leaves move while the beam is on, the leaves may be configured such that the leaf pairs in both layers of the multi-layer MLC have a larger in-layer leaf gap (than a prescribed gap determined according to a treatment plan) in order to avoid collision. Additionally, the gaps in different layers of the multi-layer MLC may be offset from each other such that an effective cross-layer leaf gap can be much smaller (e.g., 0), thereby reducing or eliminating the effect of leaf gap leakage through each layer. The MLC may include a plurality of cross-layer leaf pairs each of which includes a first leaf located in a first layer of leaves and a second leaf opposingly located in a second layer of leaves. For each of at least one of the plurality of cross-layer leaf pairs, an effective cross-layer leaf gap to be formed between the first leaf in the first layer and the second leaf in the second layer may be determined according to a treatment plan. At least one of the first leaf or the second leaf may be caused to move to form the effective cross-layer leaf gap. An in-layer leaf gap may be caused to be formed between the first leaf and an opposing first leaf that form an in-layer leaf pair in the first layer. In some embodiments, a size of the in-layer leaf gap may be no less than a threshold. The threshold may correspond to a minimum size of the in-layer leaf gap. According to embodiments of the present disclosure, in the multi-layer MLC, in-layer leaf gaps may be employed to avoid or reduce the risk of collisions between opposing leaf ends, while effective cross-layer leaf gaps may be employed to avoid or reduce radiation leakage through the multi-layer MLC. Moreover, because the risk of collision can increase with a movement speed of the leaves, a reduced danger of collision may allow for a faster movement speed of the leaves, thereby reducing the time for the treatment, facilitating a treatment planning process (e.g., by reducing the impact of motion during a session of radiation delivery), and reducing the difficulty in radiation therapy.

Figure 1:
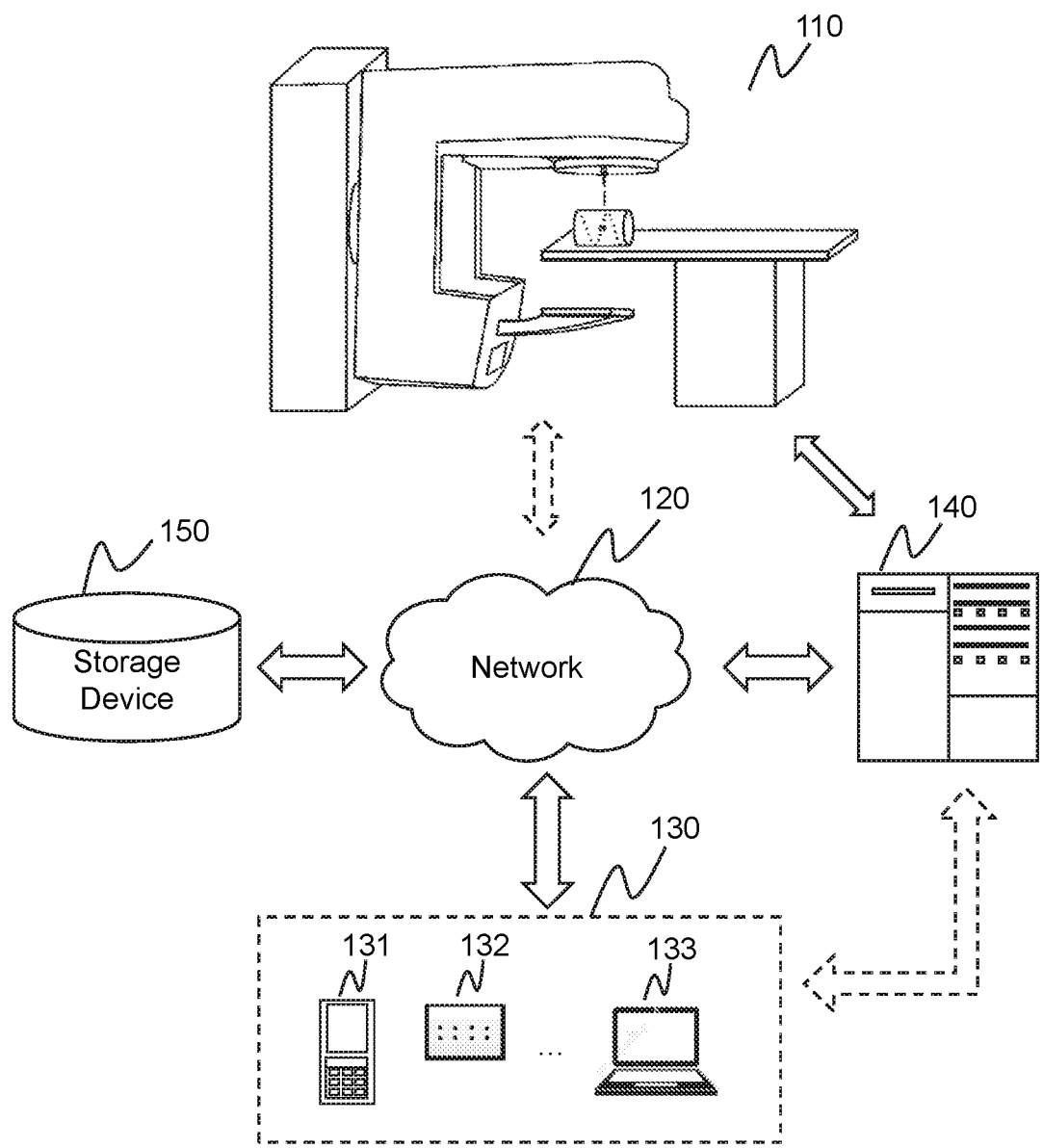
FIG. 1 is a schematic diagram illustrating an exemplary radiotherapy system according to some embodiments of the present disclosure.

FIG. 1 is a schematic diagram illustrating an exemplary radiotherapy system according to some embodiments of the present disclosure. As shown in FIG. 1, the radiotherapy system 100 may include a radiation delivery device 110, a network 120, one or more terminals 130, a processing device 140, and a storage device 150. In some embodiments, the terminal(s) 130 may be used as upper computer(s) (or host computer(s)), while the processing device 140 may be used as a lower computer (or a slave computer). The components in the radiotherapy system 100 may be connected in one or more of various ways. Merely by way of example, the radiation delivery device 110 may be connected to the processing device 140 directly (e.g., via optical fiber (e.g., a peripheral component interconnect express (PCI-E) cable)). As another example, the radiation delivery device 110 may be connected to the processing device 140 through the network 120 as indicated by the bi-directional arrow in dotted lines linking the radiation delivery device 110 and the network 120. As still another example, the storage device 150 may be connected to the processing device 140 directly or through the network 120. As still another example, the terminal 130 may be connected to the processing device 140 directly (as indicated by the bi-directional arrow in dotted lines linking the terminal 130 and the processing device 140) or through the network 120.

In some embodiments, the radiation delivery device 110 may be a radiotherapy (RT) device. In some embodiments, the RT device may deliver one or more radiation beams to a treatment region (e.g., a tumor) of an object (e.g., a patient)

for causing an alleviation of the object's symptom. In some embodiments, the RT device may be a conformal radiation therapy device, an image guided radiation therapy (IGRT) device, an intensity modulated radiation therapy (IMRT) device, an intensity modulated arc therapy (IMAT) device, or the like. In some embodiments, the RT device may include a linear accelerator (also referred to as "linac"). The linac may generate and emit a radiation beam (e.g., an X-ray beam) from a treatment head. The radiation beam may pass through one or more collimators (e.g., an MLC)) forming certain shapes, and enter into the object. In some embodiments, the radiation beam may include electrons, photons, or other types of radiation. In some embodiments, the energy of the radiation beam may be in the megavoltage range (e.g., >1 MeV), and may therefore be referred to as a megavoltage beam. The treatment head may be coupled to a gantry. The gantry may rotate, for example, clockwise or counter-clockwise around a gantry rotation axis. In some embodiments, the treatment head may rotate along with the gantry. In some embodiments, the RT device may further include a table configured to support the object during radiation treatment.

In some embodiments, the radiation delivery device 110 may further include one or more MLCs (not shown in FIG. 1). The MLC(s) may be configured to collimate radiation beam(s) of the radiation delivery device 110 and/or define the beam shape(s) thereof. In some embodiments, the MLC may include a plurality of leaves. The plurality of leaves may form an aperture. The aperture may define or modify the shape of the beam that is delivered to the object. In some embodiments, one or more leaves of the MLC may be moved according to a treatment plan. In some embodiments, the shape of the aperture may be changed according to a desired segment shape of the treatment plan. In some embodiments, the treatment plan may be generated by a treatment planning system (TPS) associated with the radiotherapy system 100.

In some embodiments, the radiation delivery device 110 may further include a drive mechanism (not shown in FIG. 1) configured to drive the leaves to move. In some embodiments, the drive mechanism may include one or more driving circuits (not shown in FIG. 1). In some embodiments, a driving circuit may generate driving signal(s) to drive the leaves of the MLC to move towards target position(s) during treatment. In some embodiments, the driving circuits may be set in the radiation delivery device 110, and may communicate with the processing device 140 via the connection between the radiation delivery device 110 and the processing device 140. For example, the processing device 140 may provide (or send) a control signal to the drive circuit, and accordingly, the drive circuit may generate a driving signal to cause, e.g., one or more actuators to drive the leaves to move towards the target position(s).

In some embodiments, the radiation delivery device 110 may further include one or more actuators configured to actuate the leaves to move. In some embodiments, an actuator may actuate the leaves to move according to a driving signal. In some embodiments, each leaf may be actuated by an actuator. Exemplary actuators may include motors, compressed gas loaded in one or more cylinders, a magnetic drive, etc. In the following descriptions, motors are described for illustration purpose; it should be noted that any other type of actuators can be used to actuate the leaves to move when using the driving methods and systems of the present disclosure.

In some embodiments, the radiation delivery device 110 may further include one or more position detection devices (not shown in FIG. 1). A position detection device may be configured to detect a current position of a leaf, and/or a current velocity of the leaf directly or indirectly. In some embodiments, the position detection device may detect a displacement of the leaf, and the current position of the leaf may be determined based on the displacement of the leaf and an initial position of the leaf, and accordingly, the current velocity of the leaf may be determined based on the displacement of the leaf and a time for the leaf movement. Exemplary position detection device(s) may include a magnetic displacement sensor (e.g., a Hall effect sensor), a grating displacement sensor, an encoder (e.g., an encoder mounted on an actuator (e.g., a motor, a cylinder, or the like)), a potentiometer (e.g., a potentiometer mounted on a motor), or the like, or any combination thereof.

In some embodiments, a leaf may have two corresponding position detection devices. For example, the leaf may have a magnetic displacement sensor and a potentiometer. The displacements of the leaf detected by the two position detection devices may be used to determine whether the leaf movement is abnormal. In some embodiments, the leaves may be configured in one or more layers. For example, the leaves may be configured in two layers, and a cross-layer leaf pair may include a first leaf located in a first layer of leaves and a second leaf oppositely located in a second layer of leaves.

In some embodiments, the current position of a leaf and/or the current velocity of the leaf may be transmitted to the processing device 140 (e.g., the control module 804) to generate control signal(s). In some embodiments, the processing device 140 may control a leaf to move based on the current position of the leaf and/or the current velocity of the leaf. In some embodiments, the current position of a leaf and/or the current velocity of the leaf may be further transmitted to the terminal(s) 130 for display.

In some embodiments, the object to be treated or scanned (also referred to as imaged) may include a body, substance, or the like, or any combination thereof. In some embodiments, the object may include a specific portion of a body, such as a head, a thorax, an abdomen, or the like, or any combination thereof. In some embodiments, the object may include a specific organ, such as a breast, an esophagus, a trachea, a bronchus, a stomach, a gallbladder, a small intestine, a colon, a bladder, a ureter, a uterus, a fallopian tube, etc.

The network 120 may include any suitable network that can facilitate exchange of information and/or data for the radiotherapy system 100. In some embodiments, one or more components of the radiotherapy system 100 (e.g., the radiation delivery device 110, the terminal(s) 130, the processing device 140, the storage device 150, etc.) may communicate information and/or data with one or more other components of the radiotherapy system 100 via the network 120. For example, the processing device 140 may obtain data corresponding to the leaves of the MLC from the radiation delivery device 110 via the network 120. As another example, the processing device 140 may obtain user instructions from the terminal(s) 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof.

Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the radiotherapy system 100 may be connected to the network 120 to exchange data and/or information.

Figure 3:
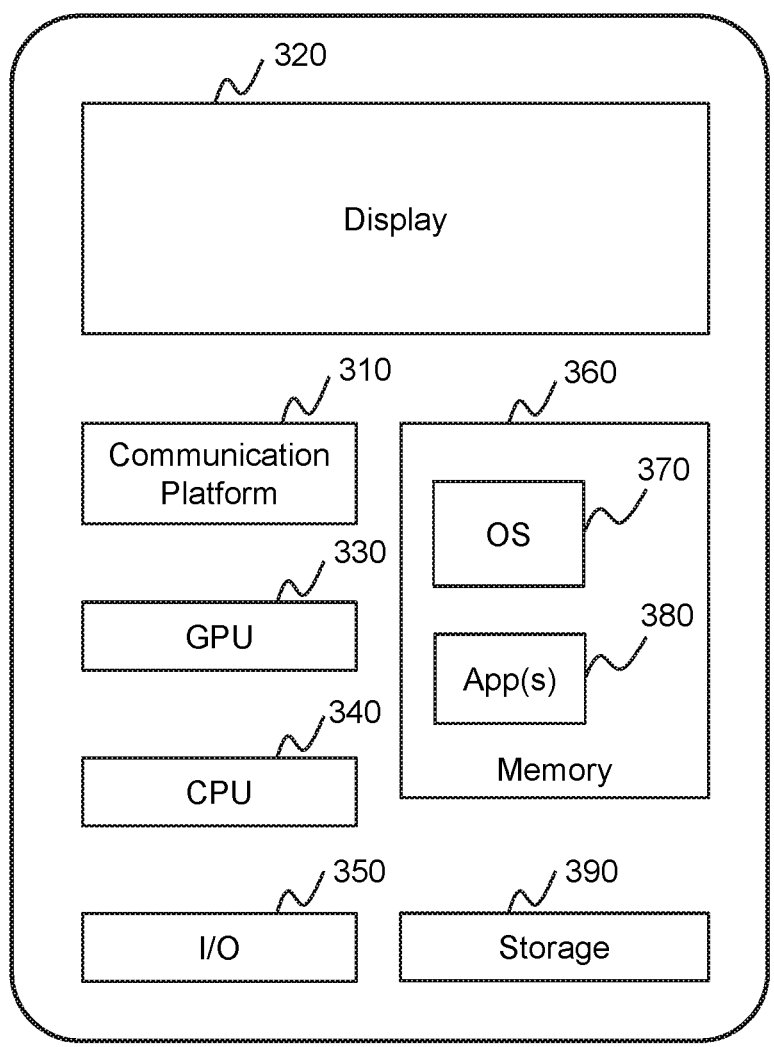
FIG. 3 is a schematic diagram illustrating exemplary hardware and/or software components of an exemplary mobile device on which the terminal may be implemented according to some embodiments of the present disclosure.

The terminal(s) 130 may enable interactions between a user and the radiotherapy system 100. The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. Merely by way of example, the terminal 130 may include a mobile device as illustrated in FIG. 3. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing device 140. In some embodiments, the terminal(s) 130 may remotely operate the radiation delivery device 110. In some embodiments, the terminal(s) 130 may operate the radiation delivery device 110 via a wireless connection. In some embodiments, the terminal(s) 130 may receive information and/or instructions inputted by a user, and send the received information and/or instructions to the radiation delivery device 110 or the processing device 140 via the network 120. In some embodiments, the terminal(s) 130 may receive data and/or information from the processing device 140. In some embodiments, the terminal(s) 130 may be part of the processing device 140. In some embodiments, the terminal(s) 130 may be omitted. In some embodiments, the terminal(s) 130 may include a control handle, a control box, a console, etc. In some embodiments, a user may choose, through the terminal(s) 130 to enable or disable the performance of the leaves illustrated in FIG. 9.

The processing device 140 may process data and/or information obtained from the radiation delivery device 110, the terminal 130, and/or the storage device 150. For example, the processing device 140 may determine an effective cross-layer leaf gap to be formed between a first leaf in a first layer and a second leaf opposingly located in a second layer, according to the treatment plan. As another example, the processing device 140 may cause at least one of the first leaf or the second leaf to move to form the effective cross-layer leaf gap. As a further example, the processing device 140 may cause an in-layer leaf gap to be formed between the first leaf and an opposing first leaf that form an in-layer leaf pair in the first layer based on the effective cross-layer leaf gap.

In some embodiments, the processing device 140 may be a computer, a user console, a single server or a server group, etc. The server group may be centralized or distributed. In some embodiments, the processing device 140 may be local or remote. For example, the processing device 140 may access information and/or data stored in the radiation delivery device 110, the terminal 130, and/or the storage device 150 via the network 120. As another example, the processing device 140 may be directly connected to the radiation delivery device 110, the terminal 130, and/or the storage device 150 to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented by a computing device 200 having one or more components as illustrated in FIG. 2.

In some embodiments, components of the radiotherapy system 100 (e.g., the radiation delivery device 110, the terminal 130, the processing device 140) may communicate with each other in a treatment process. For example, before the treatment process starts, the terminal 130 may send instruction(s) or information related to prescribed osition(s) of a leaf to the processing device 140. The processing device 140 may determine a plurality of cross-layer leaf pairs each of which includes a first leaf located in a first layer of leaves and a second leaf opposingly located in a second layer of leaves. As another example, before one or more treatment fractions start, an effective cross-layer leaf gap to be formed between the first leaf in the first layer and the second leaf in the second layer may be determined by the processing device 140, and/or stored in the terminal 130. As a further example, during the treatment process, the radiation delivery device 110 may transmit the current positions of the cross-layer leaf pairs to the processing device 140, and the processing device 140 may cause at least one of the first leaf or the second leaf to move to form the effective cross-layer leaf gap. As still a further example, the processing device 140 may transmit the current positions of the cross-layer leaf pairs to the terminal 130 for display.

The storage device 150 may store data, instructions, and/or any other information. In some embodiments, the storage device 150 may store data obtained from the radiation delivery device 110, the terminal 130 and/or the processing device 140. For example, the storage device 150 may store a treatment plan, parameters related to motion statuses of the leaves (e.g., a current position, an offset), or the like. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more other components in the radiotherapy system 100 (e.g., the processing device 140, the terminal 130, etc.). One or more components in the radiotherapy system 100 may access the data or instructions stored in the storage device 150 via the network 120. In some embodiments, the storage device 150 may be directly connected to or communicate with one or more other components in the radiotherapy system 100 (e.g., the processing device 140, the terminal 130, etc.). In some embodiments, the storage device 150 may be part of the processing device 140. In some embodiments, the processing device 140 may be connected to or communicate with the radiation delivery device 110 via the network 120, or at the backend of the processing device 140.

FIG. 2 is a schematic diagram illustrating exemplary hardware and/or software components of an exemplary computing device on which the processing device 140 may be implemented according to some embodiments of the present disclosure. As illustrated in FIG. 2, the computing device 200 may include a processor 210, a storage 220, an input/output (I/O) 230, and a communication port 240.

Figure 5:
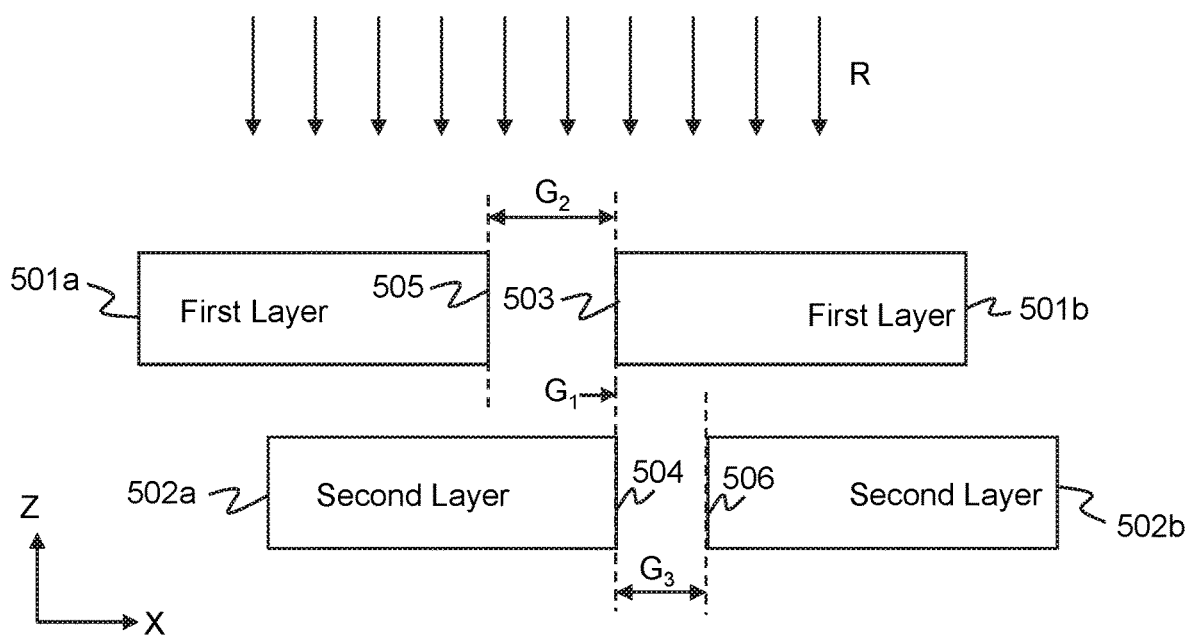
FIG. 5 is a schematic diagram illustrating an exemplary effective cross-layer leaf gap and exemplary in-layer leaf gaps according to some embodiments of the present disclosure.

The processor 210 may execute computer instructions (e.g., program code) and perform functions of the processing device 140 in accordance with techniques described herein. The computer instructions may include, for example, routines, programs, objects, components, data structures, procedures, modules, and functions, which perform particular functions described herein. For example, the processor 210 may process data obtained from the radiation delivery device 110, the terminal 130, the storage device 150, and/or any other component of the radiotherapy system 100. In some embodiments, the processor 210 may determine a plurality of cross-layer leaf pairs, each of which includes a first leaf located in a first layer of leaves and a second leaf opposingly located in a second layer of leaves. As illustrated in FIG. 5, a cross-layer leaf pair may include a first leaf located in a first layer of leaves and a second leaf opposingly located in a second layer of leaves, in which the first leaf and the second leaf have a same position on the Y-axis direction. In some embodiments, the processor 210 may determine an effective cross-layer leaf gap to be formed between the first leaf in the first layer and the second leaf in the second layer according to the treatment plan. In some embodiments, the processor 210 may cause at least one of the first leaf or the second leaf to move to form the effective cross-layer leaf gap. In some embodiments, the processor 210 may cause an in-layer leaf gap to be formed between the first leaf and an opposing first leaf that form an in-layer leaf pair in the first layer based on the effective cross-layer leaf gap. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage 220 may store data/information obtained from the radiation delivery device 110, the terminal 130, the storage device 150, and/or any other component of the radiotherapy system 100. In some embodiments, the storage 220 may include a mass storage device, a removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for driving the leaves of the MLC.

The I/O 230 may input and/or output signals, data, information, etc. In some embodiments, the I/O 230 may enable a user interaction with the processing device 140. In some embodiments, the I/O 230 may include an input device and an output device. Examples of the input device may include a keyboard, a mouse, a touch screen, a microphone, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touch screen, or the like, or a combination thereof.

The communication port 240 may be connected to a network (e.g., the network 120) to facilitate data communications. The communication port 240 may establish connections between the processing device 140 and the radiation delivery device 110, the terminal 130, and/or the storage device 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 on which the terminal 130 may be implemented according to some embodiments of the present disclosure. As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, Harmony OS, etc.) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the radiotherapy system 100 via the network 120. In some embodiments, a user may input parameters to the radiotherapy system 100, via the mobile device 300.

In order to implement various modules, units and their functions described above, a computer hardware platform may be used as hardware platforms of one or more elements (e.g., the processing device 140 and/or other components of the radiotherapy system 100 described in FIG. 1). Since these hardware elements, operating systems and program languages are common; it may be assumed that persons skilled in the art may be familiar with these techniques and they may be able to provide information needed in the imaging according to the techniques described in the present disclosure. A computer with the user interface may be used as a personal computer (PC), or other types of workstations or terminal devices. After being properly programmed, a computer with the user interface may be used as a server. It may be considered that those skilled in the art may also be familiar with such structures, programs, or general operations of this type of computing device.

Figure 4:
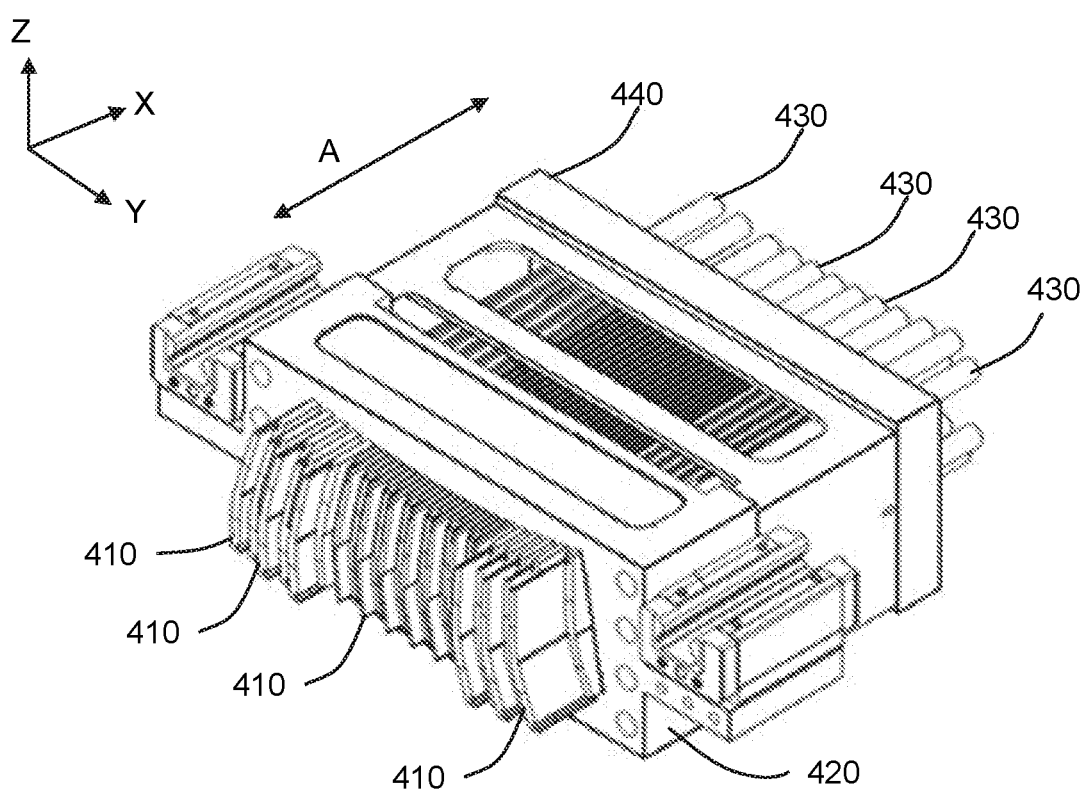
FIG. 4 is a schematic diagram illustrating a portion of an exemplary MLC according to some embodiments of the present disclosure.

FIG. 4 is a schematic diagram illustrating a portion of an exemplary MLC according to some embodiments of the present disclosure. Although only one bank of leaves are shown in FIG. 4 for illustration purposes, it should be noted that the MLC 400 may include two or more banks of leaves. For example, the MLC 400 may include two opposing banks arranged in a same layer (i.e., a same plane, or same level). As another example, the MLC 400 may include two layers of leaves (i.e., two sets of leaves in two different planes, e.g., one on top of another), and each layer may include two opposing banks. As shown in FIG. 4, the MLC 400 may include a plurality of leaves 410, a rail box 440, one or more drive mechanisms 430, and a housing 420. In some embodiments, the housing 420 may be configured to accommodate the plurality of leaves 410, the drive mechanism(s) 430, etc. In some embodiments, the housing 420 may connect with the rail box 440.

In some embodiments, the plurality of leaves 410 may be movable along a plurality of rails disposed on the rail box 440. In some embodiments, at least some leaves 410 of the plurality of leaves may be movable in a direction parallel to each another. In some embodiments, at least some of the leaves 410 may be configured to move synchronously while the radiation delivery is off. The plurality of leaves 410 may be configured to shield a portion of radiation beams and form an aperture to allow a portion of the radiation beams to pass through. The portion of the radiation beams passing through the aperture may reach a treatment region of an object to perform the radiation therapy. In some embodiments, the processing device 140 may control at least one leaf 410 of the MLC 400 to move into one or more positions to modify the shape of the aperture according to one or more parameters associated with the MLC 400 (e.g., a segment shape defined by the shape of the aperture formed by the MLC 400). The parameter(s) may be pre-determined by the processing device 140, or may be determined according to a specific condition as the specific condition occurs. Exemplary conditions may include that a scanner image of the object indicates that a position or shape of the treatment region to be treated is changed. In some embodiments, the parameter(s) may be preset in the treatment plan.

The drive mechanism(s) 430 may be configured to actuate one or more of the leaves 410 to move. In some embodiments, the drive mechanism(s) 430 may facilitate the movement of the leaves 410 such that the MLC 400 can translate the leaves 410 between a first aperture shape and a second aperture shape. In some embodiments, each leaf 410 may be capable of translating between a first position and a second position (e.g., from an open position to a closed position, from a closed position to an open position). In some embodiments, each leaf 410 may be actuated to move independently or separately from other leaves 410 of the MLC 400. In some embodiments, two or more leaves 410 may be actuated to move synchronously. In some embodiments, the drive mechanism(s) 430 may include a fluid-power drive mechanism, a spring-based drive mechanism, an electric-charge-based drive mechanism, a magnetic drive mechanism, a pneumatic drive mechanism, or the like, or a combination thereof. In some embodiments, the drive mechanism(s) 430 may include a plurality of driving motors. In some embodiments, the drive mechanism 430 may include a drive screw operably coupled to a driving motor to transmit a driving force generated by the driving motor to a corresponding leaf. The drive mechanism(s) 430 may move each leaf of the MLC 400 individually and/or independently, or may move two or more leaves together.

In some embodiments, the MLC 400 may include a plurality of the leaves 410, for example, 12, 15, 16, 24, 25, 31, 32, 36, 48, 50, 64, 72, 75, 100, 101, 120, 128, 135, etc. Merely by way of example, the MLC 400 may include 64 leaves. In some embodiments, each leaf 410 of the MLC 400 may have a width of about 1 mm to about 10 mm (e.g., about 2 mm). In some embodiments, the travel length of each leaf may be from about 0.25 cm to about 3 cm (e.g., about 1 cm). The smaller the travel range of the leaves 410 of the MLC 400 is, the more precise an aperture defined by the MLC 400 may be, and the more precisely the radiation may be delivered. However, in some embodiments, reducing leaf travel length and/or width may prolong patient treatment time. The size and shape of the leaves 410 may be at least partially determined by the geometry of a gantry, the width of the radiation beam, the distance to the radiation source (or the distance from the MLC to the target object), the target MLC penumbra, and/or the desired "resolution" at which radiation is to be applied (e.g., leaf width, number (or count) of leaves). The depth (or height) of the leaves 410 may be sufficiently thick to impede the transmission of the radiation beam when the leaves 410 are in the closed position. The depth of a leaf 410 may be the dimension of the leaf 410 along the Z-axis direction as illustrated in FIG. 4.

In some embodiments, the speed of a leaf movement may be increased by increasing the speed of the drive mechanism(s) 430. Alternatively or additionally, the MLC 400 may optionally use ball screws with a relatively wide screw pitch. In some embodiments, only a portion of the leaves 410 that shield the radiation beam may have a high atomic number material (e.g., tungsten), while the peripheral support structure(s) of the leaves 410 may include one or more lighter-weight materials. In some embodiments, a portion of a leaf 410 may be made of a substantially-radiation-impermeable material (e.g., tungsten), while the remaining portion of the leaf 410 may be made of one or more other materials (e.g., a material that is less dense and/or lighter than the substantially-radiation-impermeable material, such as stainless steel or titanium). In some embodiments, the portion of the leaf 410 made of a substantially-radiation-impermeable material may also be referred to as a substantially-radiation-impermeable portion of the leaf 410. In some embodiments, removing or hollowing out one or more regions of the leaf 410 may help to reduce the weight of the leaf 410 with little or no impact on the ability of the leaf 410 to impede radiation transmission. For example, a first section of the substantially-radiation-impermeable portion of the leaf 410 that is in the radiation path may be substantially solid, while a second section of the substantially-radiation-impermeable portion of the leaf 410 that is not in the radiation path may have one or more hollow regions.

In some embodiments, as shown in FIG. 4, the X-axis direction may refer to the longitudinal moving direction (as indicated by the arrow A) of the leaves of the MLC, the Y-axis direction may refer to the arrangement direction of adjacent leaves in a same bank of the MLC, and the Z-axis direction may be perpendicular to the X-axis direction and the Y-axis direction. In some embodiments, the X-axis direction and the Y-axis direction may be traverse to the beam direction. It should be noted that the X-axis direction, and/or Y-axis direction in the present disclosure are defined relative to the MLC. If the MLC rotates with the gantry, the actual direction of the X-axis direction, and/or Y-axis direction relative to the radiation delivery device 110 may change with the rotation of the MLC.

It should be noted that only one layer of leaves 410 are presented in FIG. 4 merely for the purposes of illustration. In some embodiments, the plurality of leaves 410 may be arranged in two or more layers. For example, the MLC 400 may include two layers, each of which includes two opposing banks. The two opposing banks of each layer may include a plurality of leaves that form a plurality of in-layer leaf pairs in the each layer. An in-layer leaf pair may include two leaves that are arranged in the two opposing banks, respectively, and are longitudinally movable relative to each other (e.g., along the X-axis direction as illustrated in FIG. 4). In some embodiments, the longitudinal moving direction may be traverse to a beam direction (e.g., along the Z-axis direction as illustrated in FIG. 4). In some embodiments, one leaf of an in-layer leaf pair in a bank may be longitudinally movable relative to the other leaf of the pair in the opposing bank.

In some embodiments, in a monolayer MLC, a portion of the in-layer leaf pairs may form an aperture shape according to the treatment plan, while other in-layer leaf pairs that are not a portion of the in-layer leaf pairs forming the aperture shape may be closed and form one or more closed in-layer leaf pairs. The closed in-layer leaf pair(s) may be configured to block at least a portion of the radiation beam impinging thereon.

According to some embodiments of the present disclosure, the MLC may include a plurality of layers of leaves. Merely by way of example, the MLC may include two layers of leaves. For illustration purposes, the descriptions below are provided with reference to a dual layer MLC. It is understood that this is not intended to be limiting. An MLC according to the systems and methods described herein may include more than two layers of leaves.

A dual layer MLC may include two layers of leaves (e.g., a first layer and a second layer), and each layer may include two opposing banks. In some embodiments, each layer of the dual layer MLC may have a similar structure to the monolayer MLC. In some embodiments, the first layer of leaves may overlap with (or be aligned with) the second layer of leaves. In some embodiments, the first layer of leaves may be set on top of the second layer of leaves. Alternatively, the second layer of leaves may be set on top of the first layer of leaves. In some embodiments, the dual layer MLC may include a plurality of cross-layer leaf pairs. A cross-layer leaf pair may include a first leaf located in the first layer of leaves and a second leaf opposingly located in the second layer of leaves. In some embodiments, at least a portion of the cross-layer leaf pairs may form an aperture according to the treatment plan, while other cross-layer leaf pairs that are not a portion of the cross-layer leaf pairs forming the aperture may be closed and form one or more closed cross-layer leaf pairs. In some embodiments, each of the cross-layer leaf pairs forming the aperture may have a corresponding effective cross-layer leaf gap according to the treatment plan. The effective cross-layer leaf gap between the first leaf and the second leaf may be formed or defined by one end of the first leaf facing an opposing first leaf in the first layer and one end of the second leaf facing an opposing second leaf in the second layer. In some embodiments, the effective cross-layer leaf gap of a cross-layer leaf pair that forms the aperture (or a portion thereof) may be larger than 0 (e.g., the effective cross-layer leaf gap $G_5$ shown in FIG. 7). In some embodiments, the effective cross-layer leaf gap for a closed cross-layer leaf pair may be substantially 0 (e.g., the effective cross-layer leaf gap $G_1$ shown in FIG. 5, the effective cross-layer leaf gap $G_4$ shown in FIG. 6). More descriptions of the effective cross-layer leaf gap may be found elsewhere in the present disclosure (e.g., FIGS. 5-7 and descriptions thereof).

In some embodiments, an in-layer leaf gap may exist between the leaves of a closed in-layer leaf pair where the leaves meet to avoid collision between leaves of a closed in-layer leaf pair. In some embodiments, at least a portion of the radiation beam impinging on the closed in-layer leaf pair may leak through the in-layer leaf gap. Using a dual layer MLC configuration, the in-layer leaf gaps in different layers may be offset with each other so that at least a portion of radiation the in-layer leaf gap in the first layer may be block by the leaf that is located in the second layer and underneath the in-layer leaf gap and the leakage through each of the in-layer leaf gaps can be reduced or eliminated. Therefore, the in-layer leaf gaps can be enlarged to avoid collisions of the in-layer leaf pairs (e.g., the closed in-layer leaf pairs).

In some embodiments, for the dual layer MLC, the plurality of leaves 410 in different layers (e.g., the first layer and the second layer) may be caused to move synchronously or asynchronously. For example, the first layer of leaves may be caused to move simultaneously with the second layer of leaves. As another example, the first layer of leaves may be caused to move before the second layer of leaves. As a further example, cross-layer leaf pairs forming effective cross-layer leaf gaps (or the aperture shape) may be caused to move before other leaves. More descriptions of the movement of the plurality of leaves 410 in the first layer and in the second layer may be found elsewhere in the present disclosure (e.g., FIGS. 5-7, and the description thereof). In some embodiments, the speed of a leaf movement may be increased by increasing the speed of the drive mechanism(s) 430. For the dual layer MLC with offset in-layer leaf gaps, because of the allowance of a relatively large in-layer leaf gap, the speed of the leaf movement may be faster, so that the adjusting time of the MLC can be reduced, and the efficiency of treatment delivery can be improved.

In some embodiments, the terms of "length," "width," "height," "side," and "end" of a leaf may be used in the description of the MLC. The "length" of a leaf as used herein may refer to a leaf dimension (e.g., in the X-axis direction) that is parallel to the leaf moving direction. The "width" of a leaf may refer to a dimension of the leaf (e.g., in the Y-axis direction) that is traverse to the leaf moving direction and the direction of the radiation beam. The "height" of a leaf may refer to a dimension of the leaf (e.g., in the Z-axis direction) substantially along the radiation beam direction. The "side" of a leaf may refer to a surface of the leaf (e.g., in the XZ plane) facing a neighboring leaf in a same bank. The "end" of a leaf may refer to a surface of the leaf (e.g., in the YZ plane) at an end of the leaf along the length of the leaf.

Figure 6:
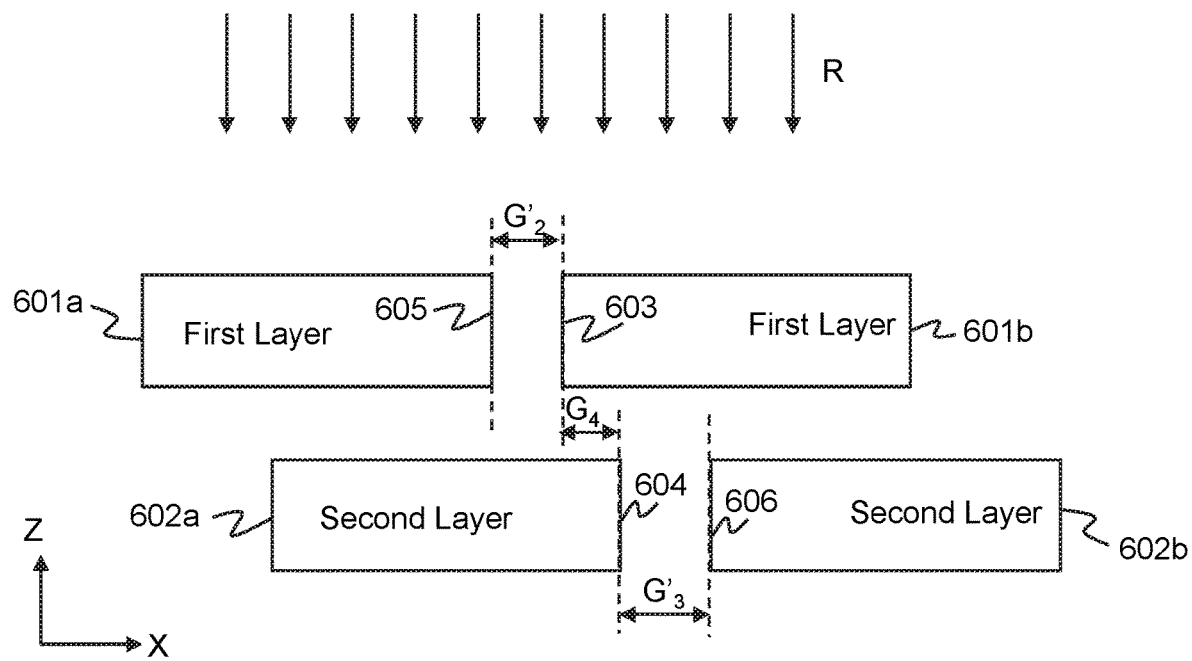
FIG. 6 is a schematic diagram illustrating another exemplary effective cross-layer leaf gap and exemplary in-layer leaf gaps according to some embodiments of the present disclosure.
Figure 7:
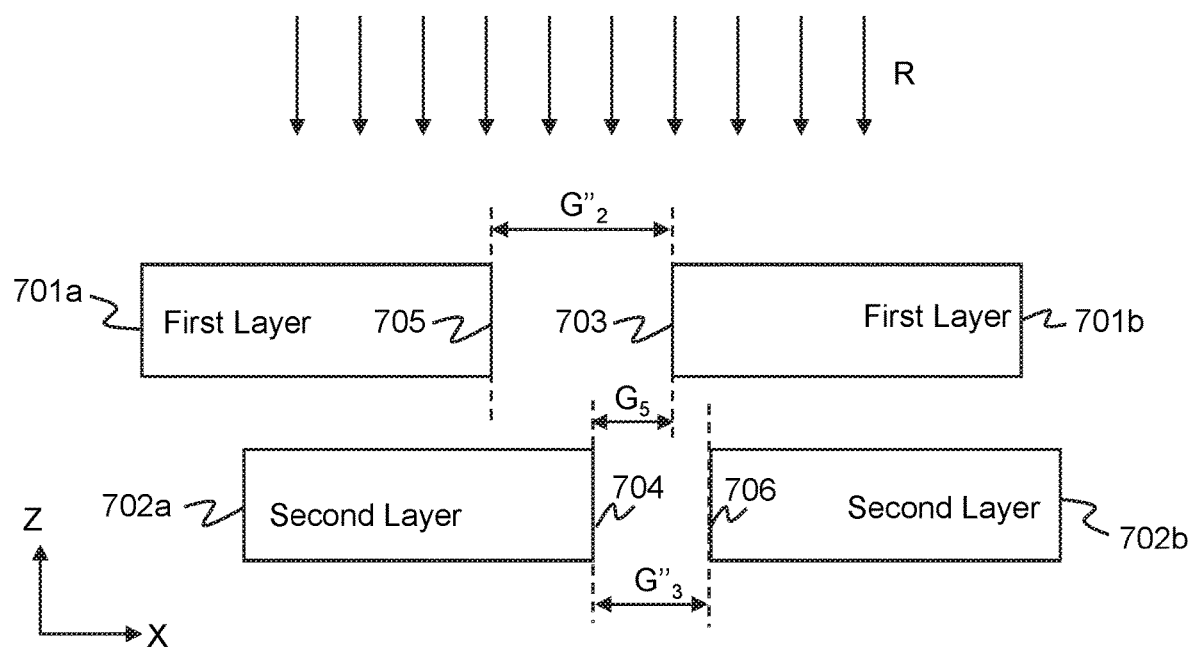
FIG. 7 is a schematic diagram illustrating another exemplary effective cross-layer leaf gap and exemplary in-layer leaf gaps according to some embodiments of the present disclosure.

In some embodiments, the leaves of the dual layer MLC exemplified in FIGS. 5-7 may have an rectangular shape. It should be noted that the rectangular cubes in FIGS. 5-7 are merely provided for the purposes of illustration, and not intended to limit the scope of the leaf in the present disclosure. In some embodiments, the leaves in the MLC may have a substantially same cross-section (e.g., a cross-section in the YZ plane). For example, the leaves in the MLC may have a same trapezoidal cross-section. The cross-section of the leaves may have other shapes including, for example, a rectangular shape, a tilted trapezoid shape, or a trapezoid with stepped or wavy ends, or the like. In some embodiments, the pattern of cross-sections of the leaves may alternate, such as trapezoid, rectangle, trapezoid, rectangle, and so on. In some embodiments, the leaf ends may be flat. In some embodiments, the neighboring leaf side surfaces may form a gap or spacing ranging from approximately 10 to 100 micrometers to facilitate relative movement between the leaves. In some embodiments, the leaf side gaps may be substantially the same. In some embodiments, the leaf end may be round, flat, or in one of various other configurations.

The arrows R shown in FIGS. 5-7 illustrate the direction of radiation beams. A radiation beam may be emitted from a radiation source. A radiation beam may include a plurality of radiation beam lets. In some embodiments, the radiation beam lets of a radiation beam may be (substantially) parallel to each other. In some embodiments, the radiation beamlets of a radiation beam may be unparallel to each other. In some embodiments, the solid arrows may indicate the radiation beam delivered from a radiation source to the leaves 501a, 501b, 502a, 502b, 601a, 601b, 602a, 602b, 701a, 701b, 702a, and 702b. The radiation beam may include a particle beam, a photon beam, an ultrasound beam (e.g., a high intensity focused ultrasound beam), or the like, or a combination thereof. The particle beam may include a stream of neutrons, protons, electrons, heavy ions, or the like, or a combination thereof. The photon beam may include an X-ray beam, a γ-ray beam, an α-ray beam, a β-ray beam, an ultraviolet beam, a laser beam, or the like, or a combination thereof. It should be noted that the incidence direction of the radiation beam perpendicular to the XY-plane in FIGS. 5-7 is merely provided for the purposes of illustration, and not intended to limit the scope of the present disclosure. For example, in some embodiments, the incidence direction of the radiation beam may form a certain angle with the XY-plane, such as 15°, 30°, 45°, 60°, 75°, or the like.

FIG. 5 is a schematic diagram illustrating an exemplary effective cross-layer leaf gap and exemplary in-layer leaf gaps according to some embodiments of the present disclosure. FIG. 6 is a schematic diagram illustrating another exemplary effective cross-layer leaf gap and exemplary in-layer leaf gaps according to some embodiments of the present disclosure. FIG. 7 is a schematic diagram illustrating another exemplary effective cross-layer leaf gap and exemplary in-layer leaf gaps according to some embodiments of the present disclosure. Although only two in-layer leaf pairs and only one cross-layer leaf pair of a dual layer MLC are shown in FIGS. 5-7 for illustration purposes, it should be noted that the dual layer MLC may include one or more in-layer leaf pairs and one or more cross-layer leaf pairs illustrated in FIGS. 5-7. As shown in FIGS. 5-7, the dual layer MLC may include two layers of leaves (e.g., the first layer and the second layer). For illustration purposes, the first layer is set on top of the second layer. In some embodiments, the second layer may be set one top of the first layer.

As shown in FIG. 5, the first layer may include a first leaf 501b and an opposing first leaf 501a that form an in-layer leaf pair in the first layer, and the second layer may include a second leaf 502a and an opposing second leaf 502b that form an in-layer leaf pair in the second layer. In some embodiments, the first leaf 501b, the opposing first leaf 501a, the second leaf 502a, and the opposing second leaf 502b may be set in different banks, respectively. In some embodiments, the first leaf 501b and the opposing second leaf 502b may be set in a same bank, and the second leaf 502a and the opposing first leaf 501a may be set in a same bank.

As shown in FIG. 6, the first layer may include a first leaf 601b and an opposing first leaf 601a that form an in-layer leaf pair in the first layer, and the second layer may include a second leaf 602a and an opposing second leaf 602b that form an in-layer leaf pair in the second layer. In some embodiments, the first leaf 601b, the opposing first leaf 601a, the second leaf 602a, and the opposing second leaf 602b may be set in different banks, respectively. In some embodiments, the first leaf 601b and the opposing second leaf 602b may be set in a same bank, and the second leaf 602a and the opposing first leaf 601a may be set in a same bank.

As shown in FIG. 7, the first layer may include a first leaf 701b and an opposing first leaf 701a that form an in-layer leaf pair in the first layer, and the second layer may include a second leaf 702a and an opposing second leaf 702b that form an in-layer leaf pair in the second layer. In some embodiments, the first leaf 701b, the opposing first leaf 701a, the second leaf 702a, and the opposing second leaf 702b may be set in different banks, respectively. In some embodiments, the first leaf 701b and the opposing second leaf 702b may be set in a same bank, and the second leaf 702a and the opposing first leaf 701a may be set in a same bank.

An effective cross-layer leaf gap may be formed between a cross-layer leaf pair (i.e., a first leaf located in the first layer and a second leaf opposingly located in the second layer (e.g., the first leaf 501b in the first layer and the second leaf 502a in the second layer as illustrated in FIG. 5, the first leaf 601b in the first layer and the second leaf 602a in the second layer as illustrated in FIG. 6, the first leaf 701b in the first layer and the second leaf 702a in the second layer as illustrated in FIG. 7)). It should be noted that the effective cross-layer leaf gap between the first leaf and the second leaf (e.g., between the first leaf 501b and the second leaf 502a, between the first leaf 601b and the second leaf 602a, between the first leaf 701b and the second leaf 702a) is merely provided for the purposes of illustration, and not intended to limit the scope of the leaf in the present disclosure. For example, the effective cross-layer leaf gap may be formed between the opposing first leaf in the first layer and the opposing second leaf in the second layer (e.g., between the opposing first leaf 501a and the opposing second leaf 502b, between the opposing first leaf 601a and the opposing second leaf 602b, between the opposing first leaf 701a and the opposing second leaf 702b). It should be noted that the effective cross-layer leaf gap may refer to a relatively small leaf gap formed between two opposing cross-layer leaf pairs, or an effective gap that radiation beams can pass through the two opposing cross-layer leaf pairs. For example, a first cross-layer leaf gap may be formed between a first leaf located in the first layer and a second leaf opposingly located in the second layer, and a second cross-layer leaf gap may be formed between the opposing first leaf in the first layer and the opposing second leaf in the second layer. If the first cross-layer leaf gap is smaller than the second cross-layer leaf gap (i.e., radiation beams can pass through the first cross-layer leaf gap), then the first cross-layer leaf gap may be designated as the effective cross-layer leaf gap. If the second cross-layer leaf gap is smaller than the first cross-layer leaf gap (i.e., radiation beams can pass through the second cross-layer leaf gap), then the second cross-layer leaf gap may be designated as the effective cross-layer leaf gap.

Specifically, as shown in FIG. 5, the effective cross-layer leaf gap $G_1$ may be formed or defined by one end 503 of the first leaf 501b facing the opposing first leaf 501a in the first layer and one end 504 of the second leaf 502a facing the opposing second leaf 502b in the second layer. As shown in FIG. 6, the effective cross-layer leaf gap $G_4$ may be formed or defined by one end 603 of the first leaf 601b facing the opposing first leaf 601a in the first layer and one end 604 of the second leaf 602a facing the opposing second leaf 602b in the second layer. As shown in FIG. 7, the effective cross-layer leaf gap $G_5$ may be formed or defined by one end 703 of the first leaf 701b facing the opposing first leaf 701a in the first layer and one end 704 of the second leaf 702a facing the opposing second leaf 702b in the second layer.

In some embodiments, the effective cross-layer leaf gap between a cross-layer leaf pair may form an aperture shape (or a portion thereof) prescribed by a treatment planning system. In some embodiments, a size of the effective cross-layer leaf gap may be determined according to a treatment plan generated by the treatment planning system. In some embodiments, the position of the aperture (i.e., the position(s) of the cross-layer leaf pair(s)) may be determined according to the treatment plan. In some embodiments, different positions may correspond to different effective cross-layer leaf gaps. In some embodiments, different positions may correspond to a same effective cross-layer leaf gap. In some embodiments, during or before radiation delivery, cross-layer leaf pair(s) may need to be moved to prescribed position(s), and effective cross-layer leaf gap(s) therebetween may need to be adjusted to prescribed size(s). In some embodiments, the position of a cross-layer leaf pair may be described in terms of a position of a portion of the cross-layer leaf pair (e.g., an end of the first leaf of the cross-layer leaf pair, an end of the second leaf of the cross-layer leaf pair, a centroid of the first leaf, a centroid of the second leaf, a center of the effective cross-layer leaf gap between the cross-layer leaf pair, etc.).

In some embodiments (e.g., in a static radiation therapy), the leaves of cross-layer leaf pair(s) may be moved to prescribed position(s) first (e.g., to form in-layer leave gap(s)), and then the effective cross-layer leaf gap(s) therebetween may be adjusted to prescribed size(s) by adjusting the position(s) of at least one leaf of the cross-layer leaf pair(s). In some embodiments (e.g., in a static radiation therapy), the effective cross-layer leaf gap(s) may be adjusted to prescribed size(s) first by adjusting the position(s) of at least one leaf of the cross-layer leaf pair(s), and then one or more leaves of the cross-layer leaf pair(s) may be moved to prescribed position(s). In some embodiments (e.g., in a dynamic radiation therapy), the movement of the cross-layer leaf pair(s) toward prescribed position(s) and the adjustment of the effective cross-layer leaf gap(s) to prescribed size(s) may be performed simultaneously or synchronously. In some embodiments, an effective cross-layer leaf gap may be adjusted to a prescribed size by causing the first leaf and/or the second leaf to move to form the effective cross-layer leaf gap. It should be noted that the descriptions of the effective cross-layer leaf gap(s) and the adjustment of the effective cross-layer leaf gap(s) in the present disclosure are not intended to limit the scope of the MLC in the present disclosure.

In some embodiments, according to the treatment plan, at certain positions (e.g., non-treatment regions (e.g., an organ at risk (OAR))) and/or in certain treatment fractions (or treatment sessions), no radiation beam (or beamlet) may need to be delivered through a certain cross-layer leaf pair. Accordingly, the effective cross-layer leaf gap of the certain cross-layer leaf pair may be prescribed as 0, i.e., the size of the effective cross-layer leaf gap is 0. In some embodiments, if the effective cross-layer leaf gap is prescribed as 0, one end of the first leaf in the first layer and one end of the second leaf in the second layer that form or define the effective cross-layer leaf gap may align with each other (e.g., along the Z-axis direction).

For example, as shown in FIG. 5, the effective cross-layer leaf gap $G_1$ is prescribed as 0, and thus, the end 503 of the first leaf 501b and the end 504 of the second leaf 502a may be aligned with each other along the Z-axis direction. In some embodiments, if the effective cross-layer leaf gap is prescribed as 0, one end of the first leaf in the first layer and one end of the second leaf in the second layer that form or define the effective cross-layer leaf gap may at least partially overlap with each other (e.g., along the X-axis direction). For example, as shown in FIG. 6, the effective cross-layer leaf gap $G_4$ is prescribed as 0, and thus, the end 603 of the first leaf 601b and the end 604 of the second leaf 602a may at least partially overlap with each other along the X-axis direction. It should be noted that in FIG. 6, even though the absolute distance between the end 603 and the end 604 in the X-axis direction is larger than 0, the effective cross-layer leaf gap $G_4$ is still considered 0 since the overlapping configuration of the first leaf 601b and the second leaf 602a along the X-axis direction can impede the transmission of the radiation beam (or beam let). In the present disclosure, if an effective cross-layer leaf gap is prescribed as 0 (either the effective cross-layer leaf gap $G_1$ in FIG. 5, or the effective cross-layer leaf gap $G_4$ in FIG. 6), it may refer that the cross-layer leaf pair that forms the effective cross-layer leaf gap is closed. If an effective cross-layer leaf gap is prescribed as larger than 0 (e.g., the effective cross-layer leaf gap $G_5$ in FIG. 7), it may refer that the cross-layer leaf pair that forms the effective cross-layer leaf gap is open.

In some embodiments, according to the treatment plan, at certain positions (e.g., treatment regions) and/or in certain treatment fractions (or treatment sessions), a radiation beam (or beam let) of a certain dose may need to be delivered through a certain cross-layer leaf pair. Accordingly, the effective cross-layer leaf gap of the certain cross-layer leaf pair may be prescribed as larger than 0, i.e., the size of the effective cross-layer leaf gap is larger than 0. The size of the effective cross-layer leaf gap may be determined according to the treatment plane. For example, as shown in FIG. 7, the effective cross-layer leaf gap $G_5$ is prescribed as larger than 0, and thus, the end 703 of the first leaf 701b and the end 704 of the second leaf 702a may be spaced apart along the X-axis direction to allow a prescribed radiation beam (or beam let) to pass through.

An in-layer leaf gap may be formed between an in-layer leaf pair (i.e., a first leaf located in the first layer and an opposing first leaf in the first layer, or a second leaf located in the second layer and an opposing second leaf in the second layer). The in-layer leaf gap between the first leaf and the opposing first leaf may be formed or defined by one end of the first leaf facing the opposing first leaf and one end of the opposing first leaf facing the first leaf. The in-layer leaf gap between the second leaf and the opposing second leaf may be formed or defined by one end of the second leaf facing the opposing second leaf and one end of the opposing second leaf facing the second leaf.

Specifically, as shown in FIG. 5, the in-layer leaf gap $G_2$ may be formed or defined by one end 503 of the first leaf 501b facing the opposing first leaf 501a in the first layer and one end 505 of the opposing first leaf 501a facing the first leaf 501b. The in-layer leaf gap $G_3$ may be formed or defined by one end 504 of the second leaf 502a facing the opposing second leaf 502b in the second layer and one end 506 of the opposing second leaf 502b facing the second leaf 502a. As shown in FIG. 6, the in-layer leaf gap $G'_2$ may be formed or defined by one end 603 of the first leaf 601b facing the opposing first leaf 601a in the first layer and one end 605 of the opposing first leaf 601a facing the first leaf 601b. The in-layer leaf gap $G'_3$ may be formed or defined by one end 604 of the second leaf 602a facing the opposing second leaf 602b in the second layer and one end 606 of the opposing second leaf 602b facing the second leaf 602a. As shown in FIG. 7, the in-layer leaf gap $G''_2$ may be formed or defined by one end 703 of the first leaf 701b facing the opposing first leaf 701a in the first layer and one end 705 of the opposing first leaf 701a facing the first leaf 701b. The in-layer leaf gap $G''_3$ may be formed or defined by one end 704 of the second leaf 702a facing the opposing second leaf 702b in the second layer and one end 706 of the opposing second leaf 702b facing the second leaf 702a.

In some embodiments, the in-layer leaf gap(s) may be adjusted according to the effective cross-layer leaf gap(s). When the effective cross-layer leaf gap is prescribed as 0 (i.e., no radiation beam (or beam let) may need to be delivered through the first leaf, the opposing first leaf, the second leaf, and the opposing second leaf), the first leaf and the second leaf that form the effective cross-layer leaf gap may be adjusted to achieve the prescribed size (i.e., 0), as shown in FIGS. 5-6. In some embodiments, the adjustment of the first leaf and the second leaf as shown in FIGS. 5-6 may reduce or prevent the passage of the radiation beam (or beamlet) through the effective cross-layer leaf gap. Therefore, theoretically, the opposing first leaf can be positioned anywhere in the X-axis direction as long as the opposing first leaf does not exceed the position of the first leaf. Similarly, the opposing second leaf can be positioned anywhere in the X-axis direction as long as the opposing second leaf does not exceed the position of the second leaf. For example, the opposing first leaf may be positioned close to the first leaf (i.e., the in-layer leaf gap therebetween may be substantially 0). As another example, the opposing first leaf may be positioned a certain distance apart from the first leaf (i.e., the in-layer leaf gap therebetween may be larger than 0 (e.g., the gaps $G_2$, $G_3$, $G'_2$, and/or $G'_3$ may be larger than 0)).

It should be noted that if two opposing leaves in a same layer are close to each other, a collision of the two opposing leaves may occur when the two opposing leaves move (especially in dynamic radiation therapy, e.g., the opposing leaves move simultaneously), thereby damaging the opposing leaves and/or the drive mechanism(s). Therefore, the first leaf and the opposing first leaf (and/or the second leaf and the opposing second leaf) may be spaced apart by at least a certain distance (e.g., a first safe distance). The first safe distance may be a minimum distance (between two opposing leaves in a same layer when the opposing leaves are moved) to avoid collisions. The first safe distance may be regarded as a first threshold. For example, the gaps $G_2$, $G_3$, $G'_2$, and/or $G'_3$ may be set larger than the first threshold. The first threshold may be set according to a default setting of the radiotherapy system 100 or preset by a user or operator via the terminals 130.

In some embodiments, the configuration of the leaves in the first layer and/or the leaves in the second layer may allow a relatively small amount of radiation leakage. For example, as shown in FIG. 5, the configuration of the second leaf 502a (e.g., the height of the second leaf 502a may be relatively small, the second leaf 502a may be made of a lighter-weight material, or the like) may allow a relatively small amount of radiation leakage when the radiation beam are delivered through the in-layer leaf gap $G_2$. Therefore, in some embodiments, the size(s) of the in-layer leaf gap(s) may be set no larger than a second threshold. The second threshold may be a second safe distance between two opposing leaves in a same layer to avoid excessive radiation leakage through the first layer and/or the second layer. The second threshold may be set according to a default setting of the radiotherapy system 100 or preset by a user or operator via the terminals 130. The second threshold may be larger than the first threshold.

When the effective cross-layer leaf gap is prescribed as larger than 0 (i.e., a radiation beam (or beam let) of a certain dose may need to be delivered through the effective cross-layer leaf gap), the first leaf and the second leaf that form the effective cross-layer leaf gap may be adjusted to achieve the prescribed size, as shown in FIG. 7. As illustrated above, the in-layer leaf gap(s) may need to satisfy the first threshold and/or the second threshold. In addition, the in-layer leaf gap(s) should not affect or change the effective cross-layer leaf gap(s). For example, as shown in FIG. 7, the opposing first leaf 701a and/or the opposing second leaf 702b should not protrude into the effective cross-layer leaf gap $G_5$, otherwise the effective cross-layer leaf gap $G_5$ may be narrowed or eliminated and may not satisfy the prescribed effective cross-layer leaf gap. That is, the in-layer leaf gap $G''_2$ (and/or the in-layer leaf gap $G''_3$) may be no less than the effective cross-layer leaf gap $G_5$.

It should be noted that the above descriptions of the effective cross-layer leaf gap(s) and in-layer leaf gap(s) in FIGS. 5-7 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the MLC may include three layers of leaves, four layers of leaves, etc. More descriptions of the adjustment of the effective cross-layer leaf gap(s) and in-layer leaf gap(s) may be found elsewhere in the present disclosure (e.g., FIG. 9 and descriptions thereof).

Figure 8:
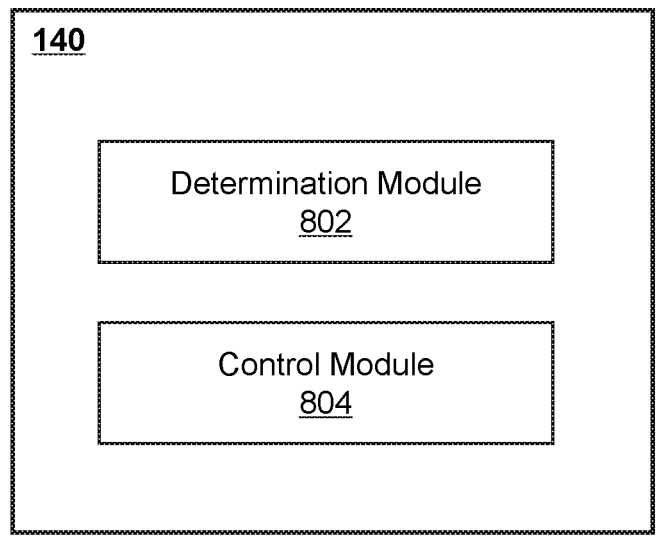
FIG. 8 is a block diagram illustrating an exemplary processing device according to some embodiments of the present disclosure.

FIG. 8 is a block diagram illustrating an exemplary processing device 140 according to some embodiments of the present disclosure. The processing device 140 may include a determination module 802 and a control module 804. At least a portion of the processing device 140 may be implemented on a computing device as illustrated in FIG. 2 or a mobile device as illustrated in FIG. 3.

In some embodiments, the determination module 802 may be configured to determine one or more effective cross-layer leaf gaps. In some embodiments, the determination module 802 may determine the effective cross-layer leaf gap(s) according to a treatment plan or a portion thereof. In some embodiments, the determination module 802 may determine the effective cross-layer leaf gap(s) at one time point in the entire treatment plan or at different time points in the entire treatment plan. More description of the determination of effective cross-layer leaf gap may be found elsewhere in the present disclosure (e.g., FIG. 9 and descriptions thereof).

In some embodiments, the control module 804 may be configured to cause one or more leaves to move to form one or more effective cross-layer leaf gaps. In some embodiments, the control module 804 may be configured to cause a first leaf and/or a second leaf to move to form a (prescribed) effective cross-layer leaf gap. In some embodiments, during or before radiation delivery (e.g., of a treatment fraction), the control module 804 may cause one or more leaves of the cross-layer leaf pair to move to prescribed position(s) to form the effective cross-layer leaf gap. More description of the forming of the effective cross-layer leaf gap may be found elsewhere in the present disclosure (e.g., FIG. 9 and descriptions thereof).

In some embodiments, the control module 804 may be configured to cause one or more leaves to move to form one or more in-layer leaf gaps. In some embodiments, the control module 804 may be configured to cause, based on the effective cross-layer leaf gap, an in-layer leaf gap to be formed or adjusted between the first leaf and an opposing first leaf that form an in-layer leaf pair in the first layer. Additionally or alternatively, the control module 804 may cause, based on the effective cross-layer leaf gap, an in-layer leaf gap to be formed or adjusted between the second leaf and an opposing second leaf that form an in-layer leaf pair in the second layer. In some embodiments, the control module 804 may cause the first in-layer leaf pair in the first layer (and/or the second in-layer leaf pair in the second layer) to be adjusted, based on the first in-layer leaf gap (and/or the second in-layer leaf gap), before or during the treatment process. The control module 804 may cause the first in-layer leaf pair in the first layer and the second in-layer leaf pair in the second layer to be adjusted synchronously or asynchronously (e.g., alternately). More description of the forming or adjustment of the in-layer leaf gap may be found elsewhere in the present disclosure (e.g., FIG. 9 and descriptions thereof).

It should be noted that the above description of the processing device 140 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the control module 804 may be divided into two units, and the effective cross-layer leaf gap(s) and the in-layer leaf gap(s) may be controlled respectively.

Figure 9:
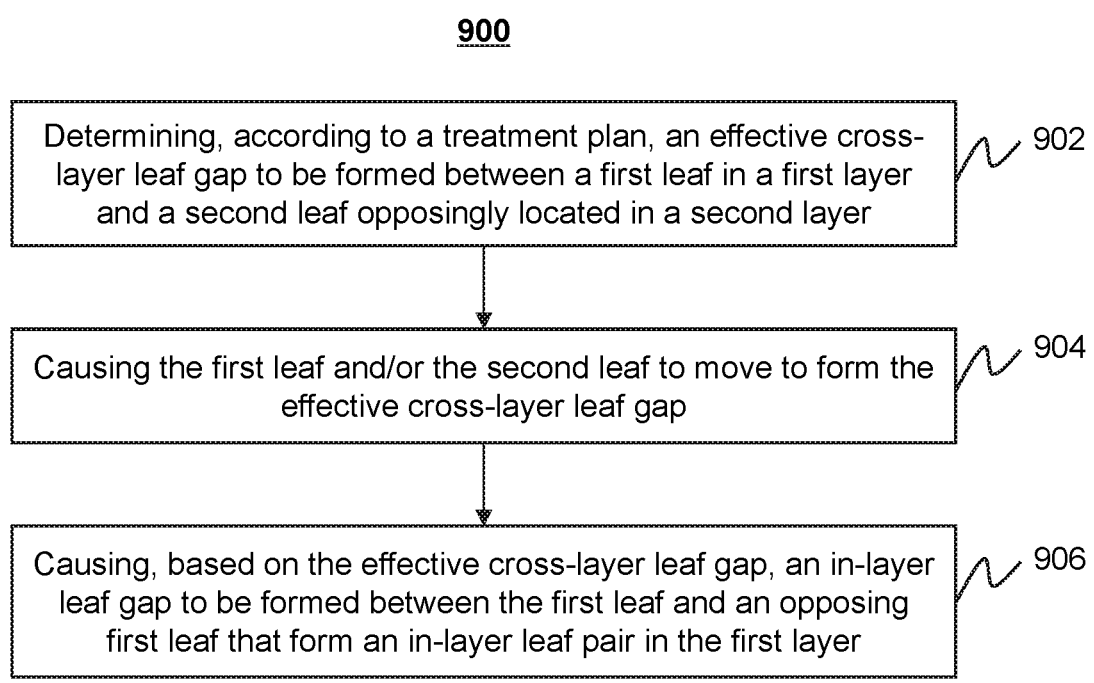
FIG. 9 is a flowchart illustrating an exemplary process for adjusting a cross-layer leaf pair of an MLC according to some embodiments of the present disclosure.

FIG. 9 is a flowchart illustrating an exemplary process for adjusting a cross-layer leaf pair of an MLC according to some embodiments of the present disclosure. Various leaves of cross-layer leaf pairs of the MLC may be adjusted according to the process. In some embodiments, one or more operations of process 900 illustrated in FIG. 9 may be performed by the processing device 140 (e.g., the control module 804). In some embodiments, one or more operations of process 900 may be implemented in the radiotherapy system 100 illustrated in FIG. 1. For example, the process 900 may be stored in the storage device 150 and/or the storage 220 in the form of instructions (e.g., an application), and invoked and/or executed by the processing device 140 (e.g., the processor 210 of the computing device 200 as illustrated in FIG. 2, the CPU 340 of the mobile device 300 as illustrated in FIG. 3, one or more modules of the processing device 140 as illustrated in FIG. 8, or the like). As another example, a portion of the process 900 may be implemented on the radiation delivery device 110. The operations of the illustrated process presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In 902, the processing device 140 (e.g., the determination module 802) may determine an effective cross-layer leaf gap. In some embodiments, the effective cross-layer leaf gap may be formed between a cross-layer leaf pair (e.g., a first leaf in a first layer and a second leaf opposingly located in a second layer of a dual layer MLC (e.g., the effective cross-layer leaf gaps $G_1$, $G_4$, and $G_5$ illustrated in FIGS. 5-7)). More descriptions of the effective cross-layer leaf gap may be found elsewhere in the present disclosure (e.g., FIGS. 5-7 and descriptions thereof).

In some embodiments, the effective cross-layer leaf gap may be determined (or prescribed) according to a treatment plan or a portion thereof. In some embodiments, before a treatment process of an object starts, a treatment plan may be generated by a treatment planning system (TPS) associated with the radiotherapy system 100. In some embodiments, the treatment plan may include information associated with the treatment process including, for example, one or more radiation parameters, a treatment dose, or the like, or a combination thereof. The radiation parameters may include radiation beam properties (e.g., a beam shape of range, an aperture shape, an intensity, a radiation direction, or the like), positions and/or directions of an object to be treated, geometric properties of the MLC, or the like. In some embodiments, a treatment process may include one or more treatment fractions (or treatment sessions). In some embodiments, after the treatment plan is generated, a user may verify and/or adjust the treatment plan to avoid potential safety hazards and/or reduce the overall duration of a treatment process. In some embodiments, the user may include a doctor, a radiation therapist, a dosimetrist, a radiation oncologist, a radiation specialist, or the like.

In some embodiments, a same cross-layer leaf pair may have different effective cross-layer leaf gaps in different positions or different treatment fractions. Although the treatment plan may be determined before the treatment process, the effective cross-layer leaf gap(s) may be determined before the treatment process or during the treatment process. In some embodiments, the effective cross-layer leaf gap(s) may be determined at one time point in the entire treatment process. Alternatively, the effective cross-layer leaf gap(s) may be determined at different time points in the entire treatment process. For example, after the treatment plan is generated and before the treatment process starts, the effective cross-layer leaf gap(s) in one or more treatment fractions may be already known according to the treatment plan, and then, the effective cross-layer leaf gap(s) in each of the one or more treatment fractions of the entire treatment process may be determined at one time. As another example, during the treatment process (e.g., before each treatment fraction), one or more effective cross-layer leaf gaps may be determined for an upcoming treatment fraction. In some embodiments, one or more first effective cross-layer leaf gaps of the same cross-layer leaf pair may be identified for a first treatment fraction before the first treatment fraction starts; one or more second effective cross-layer leaf gaps of the same cross-layer leaf pair may be determined for a second treatment fraction after the first treatment fraction is finished but before the second treatment fraction starts.

It should be noted that in some embodiments, the effective cross-layer leaf gap of a cross-layer leaf pair may be equal to 0 throughout the treatment process. For example, a cross-layer leaf pair may be closed throughout the treatment process. In some embodiments, the effective cross-layer leaf gap of a cross-layer leaf pair may be equal to 0 for one or more treatment fractions. For example, the cross-layer leaf pair may be open in a previous treatment fraction, and may be closed in a next treatment fraction. As another example, the cross-layer leaf pair may be closed in a previous treatment fraction, and may be open in a next treatment fraction. In some embodiments, the effective cross-layer leaf gap of a cross-layer leaf pair may be larger than 0 throughout the treatment process. For example, the cross-layer leaf pair may be open throughout the treatment process. In some embodiments, the effective cross-layer leaf gap(s) may change from treatment fraction to treatment fraction. In some embodiments, in a dynamic radiation therapy, the effective cross-layer leaf gap may change dynamically.

In 904, the processing device 140 (e.g., the control module 804) may cause the first leaf and/or the second leaf to move to form the (prescribed) effective cross-layer leaf gap. In some embodiments, the radiation therapy may be static. That is, the cross-layer leaf pair that form the effective cross-layer leaf gap may be static during beam delivery. In some embodiments, the first leaf and/or the second leaf in the cross-layer leaf pair may be caused to move (according to the treatment plan) to form the effective cross-layer leaf gap before the beam delivery. In some embodiments, the radiation therapy may be dynamic. That is, the first leaf and/or the second leaf in the cross-layer leaf pair that forms the effective cross-layer leaf gap may be moved during beam delivery.

In some embodiments, the size of the prescribed effective cross-layer leaf gap may be compared with 0. If the prescribed effective cross-layer leaf gap is equal to 0, the first leaf and/or the second leaf may be caused to move, so that one end of the first leaf is aligned with an opposing end of the second leaf (as illustrated in FIG. 5), or the first leaf at least partially overlaps the second leaf (as illustrated in FIG. 6). If the prescribed effective cross-layer leaf gap is larger than 0, the first leaf and/or the second leaf may be caused to move so that one end of the first leaf and an opposing end of the second leaf are spaced apart by a certain distance (i.e., the size of the prescribed effective cross-layer leaf gap) (as illustrated in FIG. 7).

In some embodiments, the position of the cross-layer leaf pair may be determined (or prescribed) according to the treatment plan. In some embodiments, different positions may correspond to different effective cross-layer leaf gaps. In some embodiments, different positions may correspond to a same effective cross-layer leaf gap. In some embodiments, during or before radiation delivery (e.g., of a treatment fraction), the cross-layer leaf pair may be caused to move to prescribed position(s). In some embodiments (e.g., in a static radiation therapy), the cross-layer leaf pair may be caused to move to prescribed position(s) first, and then the effective cross-layer leaf gap therebetween may be adjusted to prescribed size(s). In some embodiments (e.g., in a static radiation therapy), the effective cross-layer leaf gap may be adjusted to prescribed size(s) first, and then the cross-layer leaf pair may be caused to move to prescribed position(s). In some embodiments (e.g., in a dynamic radiation therapy), the movement of the cross-layer leaf pair toward prescribed position(s) and the adjustment of the effective cross-layer leaf gap to prescribed size(s) may be performed simultaneously or synchronously. For example, the first leaf and the second leaf of the cross-layer leaf pair may be caused to move simultaneously toward corresponding prescribed positions, respectively, such that when (or before) the first leaf and the second leaf reach corresponding prescribed positions, the effective cross-layer leaf gap therebetween has the prescribed size.

In 906, the processing device 140 (e.g., the control module 804) may cause, based on the effective cross-layer leaf gap, an in-layer leaf gap to be formed or adjusted between the first leaf and an opposing first leaf that form an in-layer leaf pair in the first layer. Additionally or alternatively, in some embodiments, the processing device 140 (e.g., the control module 804) may cause, based on the effective cross-layer leaf gap, an in-layer leaf gap to be formed or adjusted between the second leaf and an opposing second leaf that form an in-layer leaf pair in the second layer. An in-layer leaf pair in the first layer may also be referred to as a first in-layer leaf pair. An in-layer leaf pair in the second layer may also be referred to as a second in-layer leaf pair. More descriptions of the in-layer leaf gap may be found elsewhere in the present disclosure (e.g., FIGS. 5-7 and descriptions thereof).

In some embodiments, the radiation therapy may be static, and accordingly, at least one leaf in an in-layer leaf pair may be caused to be adjusted or moved to form the in-layer leaf gap before one or more treatment fractions (or beam deliveries). In some embodiments, the radiation therapy may be dynamic, and accordingly, the at least one leaf in the in-layer leaf pair may be caused to be adjusted or moved dynamically to form the in-layer leaf gap during one or more treatment fractions (or beam deliveries). In some embodiments, the in-layer leaf gap between the first leaf and the opposing first leaf may be caused to be formed or adjusted by causing the opposing first leaf to move relative to the first leaf (e.g., before or during the treatment process). Similarly, the in-layer leaf gap between the second leaf and the opposing second leaf may be caused to be formed or adjusted by causing the opposing second leaf to move relative to the second leaf (e.g., before or during the treatment process). In some embodiments, the processing device 140 (e.g., the control module 804) may cause a first in-layer leaf pair (or each in-layer leaf pair) in the first layer to be adjusted before or during the treatment process. In some embodiments, the processing device 140 (e.g., the control module 804) may cause a second in-layer leaf pair (or each of at least some in-layer leaf pairs) in the second layer to be adjusted before or during the treatment process. In some embodiments, an in-layer leaf pair may be adjusted by causing one or both of the leaves of the in-layer leaf pair to be moved or adjusted to form an in-layer leaf gap.

In some embodiments, operation 906 may be performed before, after, or simultaneously with operation 904. That is, the adjustment (or forming) of the in-layer leaf gap (in the first layer and/or the second layer) may be performed before, after, or simultaneously with the adjustment (or forming) of the effective cross-layer leaf gap. For example, in a static radiation therapy, the in-layer leaf pair (e.g., the first in-layer leaf pair and/or the second in-layer leaf pair) may be adjusted first, and then the cross-layer leaf pair may be adjusted. As another example, in a static radiation therapy, the cross-layer leaf pair may be adjusted first, and then the in-layer leaf pair (e.g., the first in-layer leaf pair and/or the second in-layer leaf pair) may be adjusted. As a further example, the in-layer leaf pair and the cross-layer leaf pair may be adjusted simultaneously, such that when (or before) the first leaf and the second leaf reach corresponding prescribed positions, the effective cross-layer leaf gap therebetween has a prescribed size, the in-layer leaf gap between the first leaf and the opposing first leaf is formed, and/or the in-layer leaf gap between the second leaf and the opposing second leaf is formed.

In some embodiments, in-layer leaf gaps of different in-layer leaf pairs (in a same layer or different layers) may be adjusted (i.e., in-layer leaf gaps may be caused to be formed between different in-layer leaf pairs) synchronously. In some embodiments, in-layer leaf gaps of different in-layer leaf pairs may be adjusted asynchronously. The sizes of in-layer leaf gaps of different in-layer leaf pairs may be the same or different.

In some embodiments, the in-layer leaf gap may be caused to be formed or adjusted based on the effective cross-layer leaf gap. In some embodiments, the size of the effective cross-layer leaf gap may be compared with 0, and a current size of the in-layer leaf gap may be compared with a threshold (e.g., the first threshold). In some embodiments, the first threshold may be larger than 0. In some embodiments, the first threshold may be within a range from 0.1 to 2 millimeters (such as 0.1, 0.2, 0.3, 0.4, 0.5, 0.6, 0.7, 0.8, 0.9, 1, 1.1, 1.2, 1.3, 1.4, 1.5, 1.6, 1.7, 1.8, or the like). Merely by way of example, the first threshold may be within a range from 0.2 to 0.5 millimeters.

If the size of the effective cross-layer leaf gap is equal to 0, and the current size of the in-layer leaf gap is less than the first threshold, the in-layer leaf gap between the first leaf and the opposing first leaf (also be referred to as the first in-layer leaf gap) may be caused to be adjusted to no less than the first threshold (e.g., by causing the opposing first leaf to move relative to the first leaf). For example, as shown in FIGS. 5-6, if the size of the effective cross-layer leaf gap (e.g., $G_1$ in FIG. 5, or $G_4$ in FIG. 6) is equal to 0, or the first leaf and/or the second leaf are caused to move to form the effective cross-layer leaf gap (i.e., 0), the current size of the first in-layer leaf gap (e.g., $G_2$ in FIG. 5, or $G'_2$ in FIG. 6) in the first layer may be compared with the first threshold. If the current size of the first in-layer leaf gap (e.g., $G_2$ in FIG. 5, or $G'_2$ in FIG. 6) is less than the first threshold, the first in-layer leaf gap may be caused to be adjusted to no less than the first threshold, e.g., by causing the opposing first leaf (e.g., the opposing first leaf 501a in FIG. 5, or the opposing first leaf 601a in FIG. 6) of the first in-layer leaf pair in the first layer to move relative to the first leaf (e.g., the first leaf 501b in FIG. 5, or the first leaf 601b in FIG. 6). As another example, as shown in FIGS. 5-6, if the size of the effective cross-layer leaf gap (e.g., $G_1$ in FIG. 5, or $G_4$ in FIG. 6) is equal to 0, or the first leaf and/or the second leaf are caused to move to form the effective cross-layer leaf gap (i.e., 0), the current size of the second in-layer leaf gap (e.g., $G_3$ in FIG. 5, or $G'_3$ in FIG. 6) in the second layer may be compared with the first threshold. If the current size of the second in-layer leaf gap (e.g., $G_3$ in FIG. 5, or $G'_3$ in FIG. 6) is less than the first threshold, the second in-layer leaf gap may be caused to be adjusted to no less than the first threshold, e.g., by causing the opposing second leaf (e.g., the opposing second leaf 502b in FIG. 5, or the opposing second leaf 602b in FIG. 6) of the second in-layer leaf pair in the second layer to move relative to the second leaf (e.g., the second leaf 502a in FIG. 5, or the second leaf 602a in FIG. 6).

In some embodiments, the size of the effective cross-layer leaf gap may be compared with 0, and a current size of the in-layer leaf gap may be compared with two thresholds (e.g., the first threshold as illustrated above, and the second threshold as described in FIGS. 5-7). In some embodiments, the second threshold may be within a range from 2 to 3 millimeters (such as 2, 2.1, 2.2, 2.3, 2.4, 2.5, 2.6, 2.7, 2.8, 2.9, 3, or the like). The second threshold may be larger than the first threshold.

If the size of the effective cross-layer leaf gap is equal to 0, and the current size of the in-layer leaf gap is less than the first threshold, the in-layer leaf gap between the first leaf and the opposing first leaf (also be referred to as the first in-layer leaf gap) may be caused to be adjusted to no less than the first threshold and no larger than the second threshold (e.g., by causing the opposing first leaf to move relative to the first leaf). If the size of the effective cross-layer leaf gap is equal to 0, and the current size of the in-layer leaf gap is larger than the second threshold, the in-layer leaf gap between the first leaf and the opposing first leaf (also be referred to as the first in-layer leaf gap) may be caused to be adjusted to no less than the first threshold and no larger than the second threshold (e.g., by causing the opposing first leaf to move relative to the first leaf). For example, as shown in FIGS. 5-6, if the size of the effective cross-layer leaf gap (e.g., $G_1$ in FIG. 5, or $G_4$ in FIG. 6) is equal to 0, or the first leaf and/or the second leaf are caused to move to form the effective cross-layer leaf gap (i.e., 0), the current size of the first in-layer leaf gap (e.g., $G_2$ in FIG. 5, or $G'_2$ in FIG. 6) in the first layer may be compared with the first threshold. If the current size of the first in-layer leaf gap (e.g., $G_2$ in FIG. 5, or $G'_2$ in FIG. 6) is less than the first threshold or larger than the second threshold, the first in-layer leaf gap may be caused to be adjusted to no less than the first threshold and no larger than the second threshold, e.g., by causing the opposing first leaf (e.g., the opposing first leaf 501a in FIG. 5, or the opposing first leaf 601a in FIG. 6) of the first in-layer leaf pair in the first layer to move relative to the first leaf (e.g., the first leaf 501b in FIG. 5, or the first leaf 601b in FIG. 6). Similarly, if the size of the effective cross-layer leaf gap is equal to 0, and the current size of the second in-layer leaf gap between the second leaf and the opposing second leaf in the second layer is less than the first threshold or larger than the second threshold, then the second in-layer leaf gap may be adjusted to no less than the first threshold and no larger than the second threshold.

In some embodiments, if the size of the effective cross-layer leaf gap is larger than 0, then the size of the effective cross-layer leaf gap may be compared with the first threshold. If the effective cross-layer leaf gap is no larger than the first threshold, then the in-layer leaf gap between the first leaf and the opposing first leaf (also be referred to as the first in-layer leaf gap) may be caused to be adjusted to no less than the first threshold (e.g., by causing the opposing first leaf to move relative to the first leaf). For example, as shown in FIG. 7, if the size of the effective cross-layer leaf gap (e.g., $G_5$ in FIG. 7) is larger than 0, or the first leaf and/or the second leaf are caused to move to form the effective cross-layer leaf gap $G_5$, then the size of the effective cross-layer leaf gap (e.g., $G_5$ in FIG. 7) may be compared with the first threshold. If the size of the effective cross-layer leaf gap (e.g., $G_5$ in FIG. 7) is no larger than the first threshold, then the first in-layer leaf gap may be caused to be adjusted to no less than the first threshold, e.g., by causing the opposing first leaf (e.g., the opposing first leaf 701a in FIG. 7) of the first in-layer leaf pair in the first layer to move relative to the first leaf (e.g., the first leaf 701b in FIG. 7). Similarly, if the size of the effective cross-layer leaf gap is larger than 0 and no larger than the first threshold, then the second in-layer leaf gap between the second leaf and the opposing second leaf in the second layer may be adjusted to no less than the first threshold (e.g., by causing the opposing second leaf to move relative to the second leaf). Therefore, radiation beam (or beam let) of prescribed dose can be delivered through the effective cross-layer leaf gap, and collisions between in-layer leaf pairs can be avoided.

In some embodiments, if the size of the effective cross-layer leaf gap is larger than 0 and no larger than the first threshold, then the first in-layer leaf gap (and/or the second in-layer leaf gap) may be adjusted to no less than the first threshold and no larger than the second threshold, e.g., by causing the opposing first leaf of the in-layer leaf pair in the first layer to move relative to the first leaf (and/or by causing the opposing second leaf of the in-layer leaf pair in the second layer to move relative to the second leaf). Therefore, radiation beam (or beam let) of prescribed dose can be delivered through the effective cross-layer leaf gap, collisions between in-layer leaf pairs can be avoided, and excessive radiation leakage through the in-layer leaf gap can be avoided.

In some embodiments, if the size of the effective cross-layer leaf gap is larger than 0, then the size of the effective cross-layer leaf gap may be compared with the first threshold. If the effective cross-layer leaf gap is larger than the first threshold, then the in-layer leaf gap between the first leaf and the opposing first leaf (also be referred to as the first in-layer leaf gap) may be caused to be adjusted to no less than the effective cross-layer leaf gap (e.g., by causing the opposing first leaf to move relative to the first leaf). For example, as shown in FIG. 7, if the size of the effective cross-layer leaf gap (e.g., $G_5$ in FIG. 7) is larger than 0, or the first leaf and/or the second leaf are caused to move to form the effective cross-layer leaf gap $G_5$, then the size of the effective cross-layer leaf gap (e.g., $G_5$ in FIG. 7) may be compared with the first threshold. If the size of the effective cross-layer leaf gap (e.g., $G_5$ in FIG. 7) is larger than the first threshold, then the first in-layer leaf gap may be caused to be adjusted to no less than the effective cross-layer leaf gap, e.g., by causing the opposing first leaf (e.g., the opposing first leaf 701a in FIG. 7) of the first in-layer leaf pair in the first layer to move relative to the first leaf (e.g., the first leaf 701b in FIG. 7). Similarly, if the size of the effective cross-layer leaf gap is larger than 0 and further larger than the first threshold, then the second in-layer leaf gap between the second leaf and the opposing second leaf in the second layer may be adjusted to no less than the effective cross-layer leaf gap (e.g., by causing the opposing second leaf to move relative to the second leaf). Therefore, the opposing first leaf (or the opposing second leaf) does not protrude into the effective cross-layer leaf gap, radiation beam (or beam let) of prescribed dose can be delivered through the effective cross-layer leaf gap, and collisions between in-layer leaf pairs can be avoided.

In some embodiments, if the size of the effective cross-layer leaf gap is larger than 0, then the size of the effective cross-layer leaf gap may be compared with the first threshold and the second threshold. If the effective cross-layer leaf gap is larger than the first threshold but no larger than the second threshold, then the in-layer leaf gap between the first leaf and the opposing first leaf (also be referred to as the first in-layer leaf gap) may be caused to be adjusted to no less than the effective cross-layer leaf gap and no larger than the second threshold (e.g., by causing the opposing first leaf to move relative to the first leaf). Similarly, if the size of the effective cross-layer leaf gap is larger than the first threshold but no larger than the second threshold, then the second in-layer leaf gap between the second leaf and the opposing second leaf in the second layer may be adjusted to no less than the effective cross-layer leaf gap and no larger than the second threshold (e.g., by causing the opposing second leaf to move relative to the second leaf). Therefore, the opposing first leaf (or the opposing second leaf) does not protrude into the effective cross-layer leaf gap, radiation beam (or beam let) of prescribed dose can be delivered through the effective cross-layer leaf gap, collisions between in-layer leaf pairs can be avoided, and excessive radiation leakage through the in-layer leaf gap can be avoided.

In some embodiments, if the size of the effective cross-layer leaf gap is larger than the second threshold, then the in-layer leaf gap between the first leaf and the opposing first leaf (also be referred to as the first in-layer leaf gap) may be caused to be adjusted to no less than the effective cross-layer leaf gap (e.g., by causing the opposing first leaf to move relative to the first leaf). Similarly, if the size of the effective cross-layer leaf gap is larger than the second threshold, then the second in-layer leaf gap between the second leaf and the opposing second leaf in the second layer may be adjusted to no less than the effective cross-layer leaf gap (e.g., by causing the opposing second leaf to move relative to the second leaf). Therefore, the opposing first leaf (or the opposing second leaf) does not protrude into the effective cross-layer leaf gap, radiation beam (or beam let) of prescribed dose can be delivered through the effective cross-layer leaf gap, collisions between in-layer leaf pairs can be avoided, and excessive radiation leakage through the in-layer leaf gap can be avoided.

In some embodiments, the processing device 140 (e.g., the control module 804) may cause the first in-layer leaf pair in the first layer (and/or the second in-layer leaf pair in the second layer) to be adjusted, based on the first in-layer leaf gap (and/or the second in-layer leaf gap), before or during the treatment process. In some embodiments, during the movement of the first in-layer leaf pair (or the second in-layer leaf pair), the first in-layer leaf gap (or the second in-layer leaf gap) may remain unchanged or be changed dynamically. The processing device 140 (e.g., the control module 804) may cause the first in-layer leaf pair in the first layer and the second in-layer leaf pair in the second layer to be adjusted synchronously or asynchronously (e.g., alternately).

In some embodiments, in a treatment process, one or more leaves of cross-layer leaf pairs and/or one or more leaves of in-layer leaf pairs of the MLC may be adjusted or moved. In some embodiments, an effective cross-layer leaf gap may be formed between the first leaf in the first layer and the second leaf in the second layer. In some embodiments, an in-layer leaf gap may be formed between the first leaf and the opposing first leaf that form an in-layer leaf pair in the first layer. In some embodiments, the size of the in-layer leaf gap may be no less than the size of the effective cross-layer leaf gap. In some embodiments, the size of the in-layer leaf gap may be no less than the first threshold and no larger than the second threshold. In some embodiments, the size of the in-layer leaf gap may be determined based on a random value. For example, the size of the in-layer leaf gap may have a random value. In some embodiments, the size of the in-layer leaf gap may have a fixed value when the size of the effective cross-layer leaf gap is 0. In some embodiments, the size of the in-layer leaf gap may be equal to a sum of a fixed value and the size of the effective cross-layer leaf gap. In some embodiments, the size of the in-layer leaf gap may be equal to the size of the effective cross-layer leaf gap when the size of the effective cross-layer leaf gap is no less than a third threshold. In some embodiments, the third threshold may be larger than 0. In some embodiments, the third threshold may be no less than the first threshold and/or no larger than the second threshold. In some embodiments, the third threshold may be larger than the second threshold.

It should be noted that the above descriptions of the process 900 are merely provided for the purposes of illustration, and not intended to limit the scope of the present disclosure. For persons having ordinary skill in the art, multiple variations and modifications may be made under the teachings of the present disclosure. However, those variations and modifications do not depart from the scope of the present disclosure. In some embodiments, at least one in-layer leaf pair or cross-layer leaf pair of the leaves in the MLC may be caused to move according to the process 900. In some embodiments, two or more in-layer leaf pairs or cross-layer leaf pairs of the MLC may be moved according to the process 900 synchronously or alternately. In some embodiments, the process 900 may be repeated to form two or more effective cross-layer leaf gaps for a same cross-layer leaf pair (or form two or more in-layer leaf gaps for a same in-layer leaf pair) for a radiation treatment.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in a combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, for example, an installation on an existing server or mobile device.

Similarly, it should be appreciated that in the foregoing description of embodiments of the present disclosure, various features are sometimes grouped in a single embodiment, figure, or descriptions thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method implemented on at least one machine, each machine of the at least one machine has at least one processor and at least one storage device for adjusting a multi-leaf collimator (MLC) in a treatment process, the MLC including a plurality of cross-layer leaf pairs, each cross-layer leaf pair of the plurality of cross-layer leaf pairs includes a first leaf located in a first layer of leaves and a second leaf opposingly located in a second layer of leaves, the method comprising:

for each cross-layer leaf pair of at least one of the plurality of cross-layer leaf pairs,
determining, according to a treatment plan, an effective cross-layer leaf gap to be formed between the first leaf in the first layer and the second leaf in the second layer;
causing at least one of the first leaf in the first layer or the second leaf in the second layer to move to form the effective cross-layer leaf gap; and
causing, based on the effective cross-layer leaf gap, an in-layer leaf gap to be formed between the first leaf in the first layer and an opposing first leaf in the first layer of the MLC, the first leaf and the opposing first leaf forming an in-layer leaf pair in the first layer,
wherein a size of the in-layer leaf gap is no less than a threshold.

2. The method of claim 1, wherein for each cross-layer leaf pair of at least one of the plurality of cross-layer leaf pairs, the causing, based on the effective cross-layer leaf gap, an in-layer leaf gap to be formed between the first leaf and an opposing first leaf that form an in-layer leaf pair in the first layer further comprises:
comparing a size of the effective cross-layer leaf gap with 0.

3. The method of claim 2, wherein for each cross-layer leaf pair of at least one of the plurality of cross-layer leaf pairs, the causing, based on the effective cross-layer leaf gap, an in-layer leaf gap to be formed between the first leaf and an opposing first leaf that form an in-layer leaf pair in the first layer further comprises:
in response to determining that the size of the effective cross-layer leaf gap is equal to 0,
comparing the size of the in-layer leaf gap with the threshold; and
in response to determining that the size of the in-layer leaf gap is less than the threshold, causing the in-layer leaf gap to be adjusted to no less than the threshold, by causing the opposing first leaf of the in-layer leaf pair in the first layer to move relative to the first leaf.

4. The method of claim 2, wherein for each cross-layer leaf pair of at least one of the plurality of cross-layer leaf pairs, the causing, based on the effective cross-layer leaf gap, an in-layer leaf gap to be formed between the first leaf and an opposing first leaf that form an in-layer leaf pair in the first layer further comprises:

in response to determining that the size of the effective cross-layer leaf gap is equal to 0,
    comparing the size of the in-layer leaf gap with the threshold; and
    in response to determining that the size of the in-layer leaf gap is less than the threshold, causing the in-layer leaf gap to be adjusted to no less than the threshold and no larger than a second threshold, by causing the opposing first leaf of the in-layer leaf pair in the first layer to move relative to the first leaf.

5. The method of claim 2, wherein for each cross-layer leaf pair of at least one of the plurality of cross-layer leaf pairs, the causing, based on the effective cross-layer leaf gap, an in-layer leaf gap to be formed between the first leaf and an opposing first leaf that form an in-layer leaf pair in the first layer further comprises:
    in response to determining that the size of the effective cross-layer leaf gap is larger than 0,
        comparing the size of the effective cross-layer leaf gap with the threshold; and
        in response to determining that the size of the effective cross-layer leaf gap is no larger than the threshold, causing the in-layer leaf gap to be adjusted to no less than the threshold, by causing the opposing first leaf of the in-layer leaf pair in the first layer to move relative to the first leaf.

6. The method of claim 2, wherein for each cross-layer leaf pair of at least one of the plurality of cross-layer leaf pairs, the causing, based on the effective cross-layer leaf gap, an in-layer leaf gap to be formed between the first leaf and an opposing first leaf that form an in-layer leaf pair in the first layer further comprises:
    in response to determining that the size of the effective cross-layer leaf gap is larger than 0,
        comparing the size of the effective cross-layer leaf gap with the threshold; and
        in response to determining that the size of the effective cross-layer leaf gap is larger than the threshold, causing the in-layer leaf gap to be adjusted to no less than the effective cross-layer leaf gap, by causing the opposing first leaf of the in-layer leaf pair in the first layer to move relative to the first leaf.

7. The method of claim 2, wherein for each cross-layer leaf pair of at least one of the plurality of cross-layer leaf pairs, the causing, based on the effective cross-layer leaf gap, an in-layer leaf gap to be formed between the first leaf and an opposing first leaf that form an in-layer leaf pair in the first layer further comprises:
    in response to determining that the size of the effective cross-layer leaf gap is larger than 0,
        comparing the size of the effective cross-layer leaf gap with the threshold; and
        in response to determining that the size of the effective cross-layer leaf gap is no larger than the threshold, causing the in-layer leaf gap to be adjusted to no less than the threshold and no larger than a second threshold, by causing the opposing first leaf of the in-layer leaf pair in the first layer to move relative to the first leaf.

8. The method of claim 2, wherein for each cross-layer leaf pair of at least one of the plurality of cross-layer leaf pairs, the causing, based on the effective cross-layer leaf gap, an in-layer leaf gap to be formed between the first leaf and an opposing first leaf that form an in-layer leaf pair in the first layer further comprises:
    in response to determining that the size of the effective cross-layer leaf gap is larger than 0,
        comparing the size of the effective cross-layer leaf gap with the threshold and a second threshold; and
        in response to determining that the size of the effective cross-layer leaf gap is larger than the threshold but no larger than the second threshold, causing the in-layer leaf gap to be adjusted to no less than the effective cross-layer leaf gap and no larger than the second threshold, by causing the opposing first leaf of the in-layer leaf pair in the first layer to move relative to the first leaf.

9. The method of claim 2, wherein for each cross-layer leaf pair of at least one of the plurality of cross-layer leaf pairs, the causing, based on the effective cross-layer leaf gap, an in-layer leaf gap to be formed between the first leaf and an opposing first leaf that form an in-layer leaf pair in the first layer further comprises:
    in response to determining that the size of the effective cross-layer leaf gap is larger than 0,
        comparing the size of the effective cross-layer leaf gap with a second threshold; and
        in response to determining that the size of the effective cross-layer leaf gap is larger than the second threshold, causing the in-layer leaf gap to be adjusted to no less than the effective cross-layer leaf gap, by causing the opposing first leaf of the in-layer leaf pair in the first layer to move relative to the first leaf.

10. The method of claim 1, further comprising:
    causing, based on the effective cross-layer leaf gap, a second in-layer leaf gap to be formed between the second leaf and an opposing second leaf that form a second in-layer leaf pair in the second layer.

11. The method of claim 10, wherein the causing, based on the effective cross-layer leaf gap, a second in-layer leaf gap to be formed between the second leaf and an opposing second leaf that form a second in-layer leaf pair in the second layer comprises:
    in response to determining that a size of the effective cross-layer leaf gap is larger than 0,
        comparing the size of the effective cross-layer leaf gap with the threshold;
        in response to determining that the size of the effective cross-layer leaf gap is no larger than the threshold,
            causing the second in-layer leaf gap to be adjusted to no less than the threshold, by causing the opposing second leaf of the second in-layer leaf pair in the second layer to move relative to the second leaf; and
            causing the in-layer leaf gap to be adjusted to no less than the threshold, by causing the opposing first leaf of the in-layer leaf pair in the first layer to move relative to the first leaf.

12. The method of claim 10, wherein the causing, based on the effective cross-layer leaf gap, a second in-layer leaf gap to be formed between the second leaf and an opposing second leaf that form a second in-layer leaf pair in the second layer comprises:
    in response to determining that a size of the effective cross-layer leaf gap is larger than 0,
        comparing the size of the effective cross-layer leaf gap with the threshold;
        in response to determining that the size of the effective cross-layer leaf gap is larger than the threshold,
            causing the second in-layer leaf gap to be adjusted to no less than the effective cross-layer leaf gap, by causing the opposing second leaf of the second in-layer leaf pair in the second layer to move relative to the second leaf; and causing the in-layer leaf gap to be adjusted to no less than the effective cross-layer leaf gap, by causing the opposing first leaf of the in-layer leaf pair in the first layer to move relative to the first leaf.

13. The method of claim 10, further comprising:
for the each cross-layer leaf pair of at least one of the plurality of cross-layer leaf pairs, causing at least one of the in-layer leaf pair in the first layer or the second in-layer leaf pair in the second layer to be adjusted before or during the treatment process by:
causing, based on at least one of the in-layer leaf gap or the second in-layer leaf gap, the in-layer leaf pair in the first layer and the second in-layer leaf pair in the second layer to be adjusted synchronously.

14. The method of claim 1, further comprising:
for the each cross-layer leaf pair of at least one of the plurality of cross-layer leaf pairs, causing the in-layer leaf pair in the first layer to be adjusted before or during the treatment process.

15. The method of claim 1, wherein the threshold is larger than 0.

16. The method of claim 1, wherein the threshold is within a range from 0.1 to 2 millimeters.

17. The method of claim 1, wherein in response to determining that a size of the effective cross-layer leaf gap is equal to 0, the in-layer leaf gap is no larger than a second threshold.

18. The method of claim 17, wherein the second threshold is within a range from 2 to 3 millimeters.

19. A system for adjusting a multi-leaf collimator (MLC) in a treatment process, the MLC including a plurality of cross-layer leaf pairs and a plurality of in-layer leaf pairs, each cross-layer leaf pair of the plurality of cross-layer leaf pairs includes a first leaf located in a first layer of leaves and a second leaf opposingly located in a second layer of leaves, and each in-layer leaf pair of the plurality of in-layer leaf pairs includes the first leaf located in the first layer and an opposing first leaf that is opposingly located in the first layer, the system comprising:
at least one storage device storing a set of instructions; and
at least one processor in communication with the at least one storage device, wherein when executing the set of instructions, the at least one processor is configured to perform operations including:
for each cross-layer leaf pair of at least one of the plurality of cross-layer leaf pairs,
determining, according to a treatment plan, an effective cross-layer leaf gap to be formed between the first leaf in the first layer and the second leaf in the second layer;
causing at least one of the first leaf in the first layer or the second leaf in the second layer to move to form the effective cross-layer leaf gap; and
causing, based on the effective cross-layer leaf gap, an in-layer leaf gap to be formed between the first leaf in the first layer and the opposing first leaf in the first layer of the MLC,
wherein a size of the in-layer leaf gap is no less than a threshold.

20. A non-transitory computer-readable medium storing instructions, the instructions, when executed by at least one processor, causing the at least one processor to implement a method comprising:
for each cross-layer leaf pair of at least one of a plurality of cross-layer leaf pairs of a multi-leaf collimator (MLC), each cross-layer leaf pair of the plurality of cross-layer leaf pairs includes a first leaf located in a first layer of leaves of the MLC and a second leaf opposingly located in a second layer of leaves of the MLC,
determining, according to a treatment plan, an effective cross-layer leaf gap to be formed between the first leaf in the first layer and the second leaf in the second layer;
causing at least one of the first leaf in the first layer or the second leaf in the second layer to move to form the effective cross-layer leaf gap; and
causing, based on the effective cross-layer leaf gap, an in-layer leaf gap to be formed between the first leaf in the first layer and an opposing first leaf in the first layer of the MLC, the first leaf and the opposing first leaf forming an in-layer leaf pair in the first layer,
wherein a size of the in-layer leaf gap is no less than a threshold.

* * * * *